(12) United States Patent
Dalton et al.

(10) Patent No.: US 6,787,090 B2
(45) Date of Patent: Sep. 7, 2004

(54) METHOD OF PRODUCING STRUCTURES USING CENTRIFUGAL FORCES

(75) Inventors: Paul D. Dalton, Toronto (CA); Molly S. Shoichet, Toronto (CA)

(73) Assignee: matRegen Corp., Toronto (CA)

( * ) Notice: Subject to any disclaimer, the term of this patent is extended or adjusted under 35 U.S.C. 154(b) by 0 days.

(21) Appl. No.: 10/169,948

(22) PCT Filed: May 11, 2001

(86) PCT No.: PCT/CA01/00680
§ 371 (c)(1),
(2), (4) Date: Jul. 11, 2002

(87) PCT Pub. No.: WO01/85417
PCT Pub. Date: Nov. 15, 2001

(65) Prior Publication Data
US 2003/0039777 A1 Feb. 27, 2003

Related U.S. Application Data
(60) Provisional application No. 60/203,910, filed on May 12, 2000.

(51) Int. Cl.[7] .................................................. B29C 39/08
(52) U.S. Cl. ........................ 264/255; 264/267; 264/310; 264/311; 264/349
(58) Field of Search .............................. 264/53, 310, 311, 264/255, 267, 349

(56) References Cited

U.S. PATENT DOCUMENTS

| | | | |
|---|---|---|---|
| 3,870,775 A | * 3/1975 | Castro et al. | 264/53 |
| 4,666,640 A | * 5/1987 | Neefe | 264/2.1 |
| 5,182,052 A | * 1/1993 | Lydtin et al. | 264/1.2 |
| 5,250,240 A | 10/1993 | Kim et al. | |
| 5,266,325 A | 11/1993 | Kuzma et al. | |
| 5,292,515 A | 3/1994 | Moro et al. | |
| 5,532,282 A | * 7/1996 | Needham | 521/93 |
| 5,868,976 A | 2/1999 | Puglia et al. | |
| 6,090,486 A | * 7/2000 | Riffle et al. | 428/373 |
| 6,589,470 B2 | * 7/2003 | Fried et al. | 264/443 |

FOREIGN PATENT DOCUMENTS

| | | |
|---|---|---|
| DE | 1514410 | 10/1969 |
| GB | 2003108 | 3/1979 |
| JP | 63075645 | 3/1988 |
| JP | 04348117 | 12/1992 |

* cited by examiner

Primary Examiner—Stefan Stancovici
(74) Attorney, Agent, or Firm—Lynn C. Schumacher; Hill & Schumacher

(57) ABSTRACT

Hollow polymeric structures with unique morphologies are manufactured with a rotational spinning technique wherein phase separation of soluble solutions is induced within a filled mold as it is rotated. As phase-separation occurs, an increase in density of one phase results in sediment at a periphery under centrifugal forces and after or during sedimentation, gelation of phase-separated particles fixes a tube morphology. By controlling the rotational speed and the formulation chemistry, the tube dimensions and wall morphology can be manipulated. The method requires small quantities of starting material, permits multi-layering of tubes, is applicable to diverse polymers and results in highly diffusive hollow structures while maintaining good mechanical strength.

42 Claims, 19 Drawing Sheets

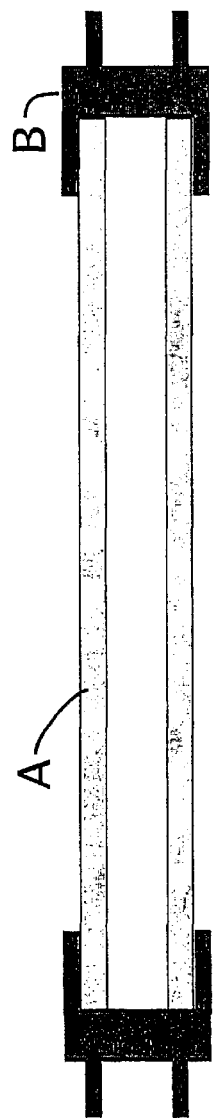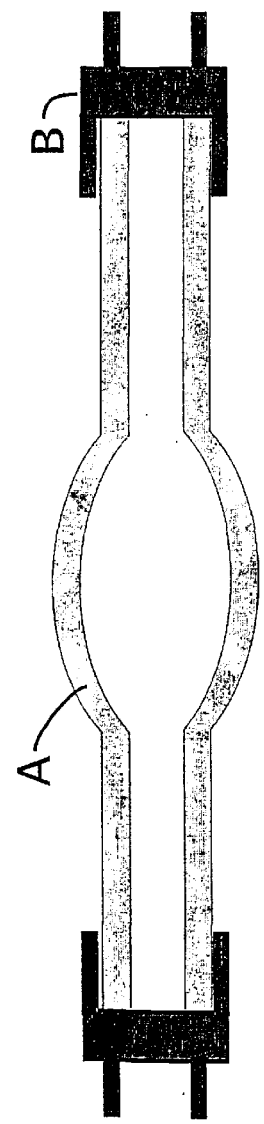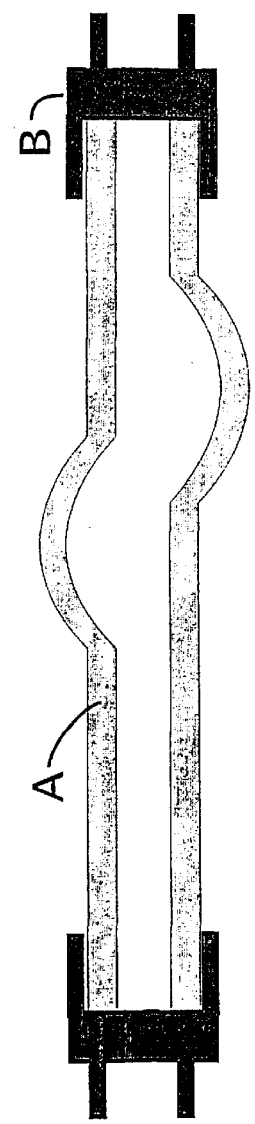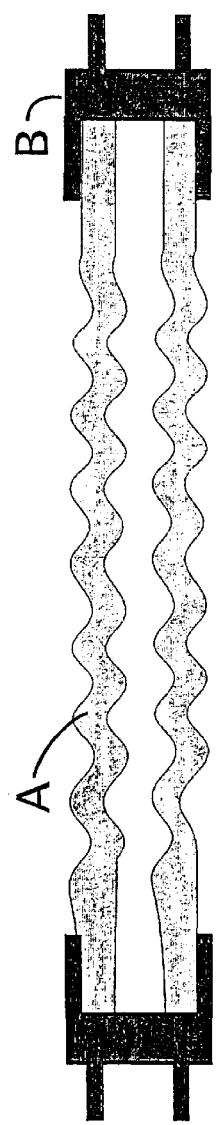

E   A

J   K

Fig.8a
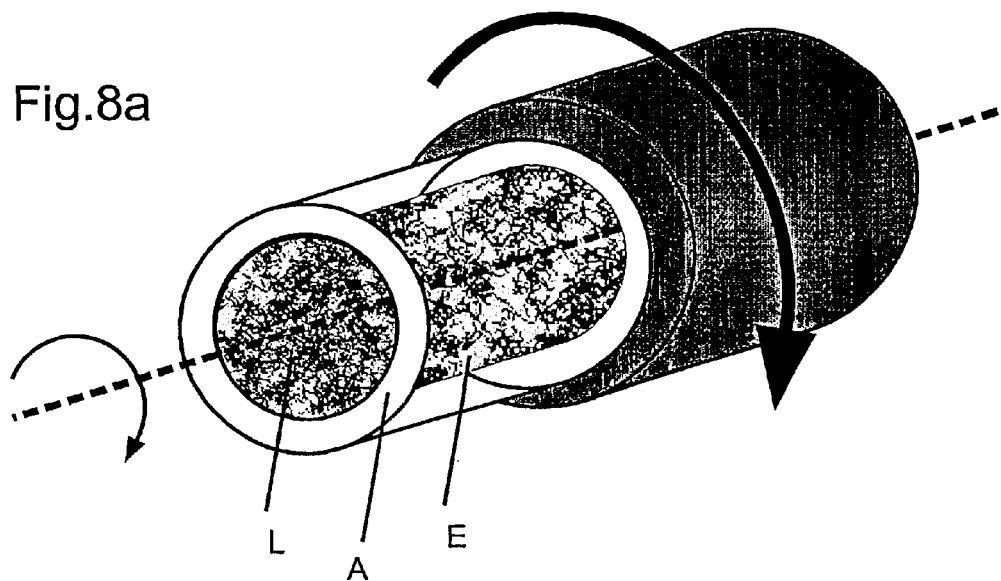
PHEMA-coated porous PLGA
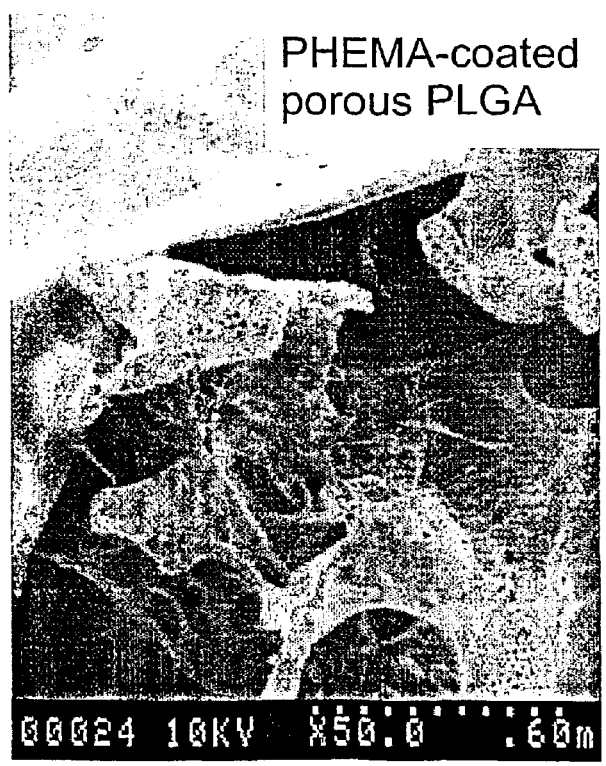
Fig.8b

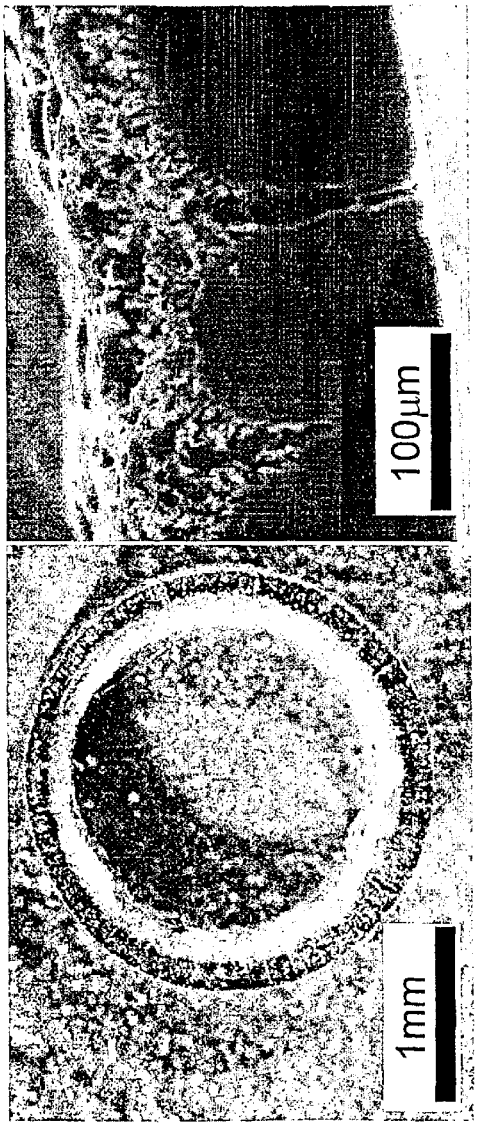
Fig.12a
Fig.12b
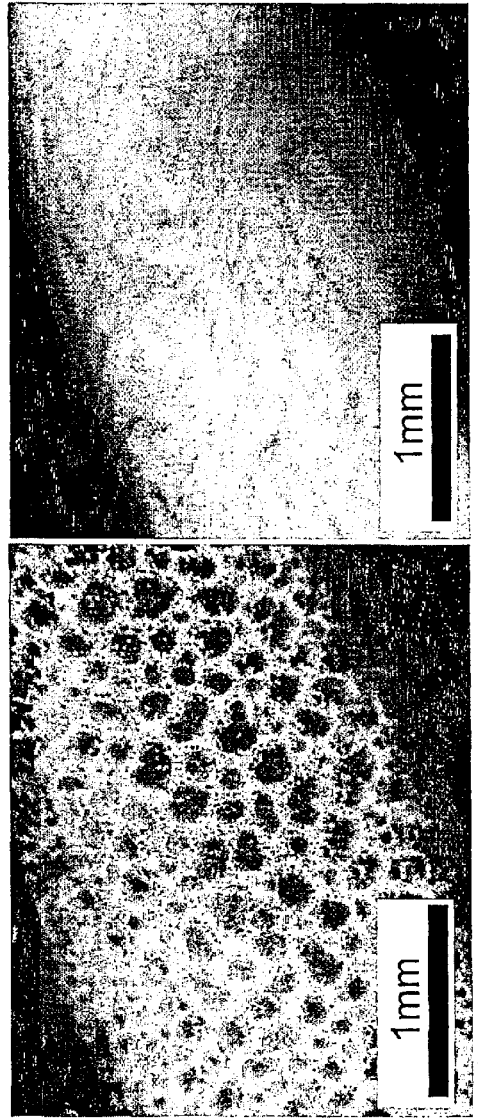
Fig.12c
Fig.12d

METHOD OF PRODUCING STRUCTURES USING CENTRIFUGAL FORCES

CROSS REFERENCE TO RELATED APPLICATIONS

This application is a National Phase application claiming the benefit of PCT/CA01/00680 filed May 11, 2002 which further claims priority benefit from U.S. provisional patent application No. 60/203,910 filed May 12, 2000.

FIELD OF INVENTION

This invention relates to a method of manufacturing structures and particularly polymeric tubular structures with complex and unique morphologies in the walls, and on the inner and outer surfaces of the structures.

BACKGROUND OF THE INVENTION

Tubular structures have been prepared by a number of techniques, each of which has limitations for each application. For biomedical applications, a limitation is the abundant material required to prepare structures of limited size and shape, which can prove costly. For porous polymeric tubes, also known as hollow fiber membranes (HFMs), tubes with wall thicknesses on the order of hundreds of microns are prepared. There is no suitable method to prepare concentric, long HFMs, with thin walls, whether by dip-coating, spinning, or centrifugal casting, among others. As will be described in more detail, the invention comprises a process to prepare HFMs, or any hollow structure, with a broad range of wall and surface morphologies, dimensions and shapes. Such wall morphologies allow HFMs to be manufactured with considerably different transport properties while maintaining similar mechanical properties.

HFMs are commonly prepared by phase inversion through an annular die (or spinneret) where the solvent/non-solvent system controls many of the resulting properties, such as morphology of the wall structure. The dimensions are controlled by the spinneret, which must be finely tuned for concentricity. While the spinning technique has a proven record commercially, it requires abundant material and requires a certain amount of art to prepare reproducible HFMs.

Centrifugal casting is a process used to make a wide number of structures, both tubular and non-concentric (U.S. Pat. Nos. 5,266,325; 5,292,515). For manufacturing tubular shapes, a cylindrical mold is partially filled with a monomer, polymer melt, or monomer solution, and with air present inside the mold, coats the periphery of the mold under centrifugal action. The material spun to the outer portion of the mold is then held in place using temperature changes (cooling), polymerization or evaporation of the solvent. For this process, two phases are present inside the mold (air and liquid) before rotation; phase separation is not necessary for tubular formation. Wall morphologies are only attained by the addition of a porogen (salt, ethylene glycol etc.) that is leached out post-polymerization. Since air is required in the mold to form a tube (compared to a rod), attaining small diameter tubes with a small inner diameter on the micron scale cannot be achieved. Surface tension between the liquid and the gas inside the mold prevents miniaturization of the inner diameters for tens of centimeter length tubes.

For dip-coating, tubes are formed around a mandrel that is sequentially dipped in a polymer solution and non-solvent system, thereby coating the mandrel with the polymer via a phase inversion process. Alternately, the mandrel may be dipped in a polymer solution and the solvent left to evaporate. By these methods, the uniformity of the tube wall along the length of the tube is not well controlled.

It would therefore be very advantageous to manufacture tubes within a size regime, concentricity and with a multi-layering capability that is not presently achievable with the aforementioned methods.

SUMMARY OF INVENTION

The present invention provides a process of producing a product, comprising:

a) filling an interior of a mold with a solution so that substantially all air is displaced therefrom, the solution comprising at least two components which can be phase separated by a phase separation agent into at least two phases;

b) rotating said mold containing said solution at an effective rotational velocity in the presence of said phase separation agent to induce phase separation between said at least two components into at least two phases so that under rotation at least one of the phases deposits onto an inner surface of the mold; and c) forming said product by stabilizing said at least one of the phases deposited onto the inner surface of the mold.

The present invention provides a product produced by the method, comprising:

a) filling an interior of a mold with a solution so that substantially all air is displaced therefrom, the solution comprising at least two components which can be phase separated by a phase separation agent into at least two phases;

b) rotating said mold containing said solution at an effective rotational velocity in the presence of said phase separation agent to induce phase separation between said at least two components into at least two phases so that under rotation at least one of the phases deposits onto an inner surface of the mold; and c) forming said product by stabilizing said at least one of the phases deposited onto the inner surface of the mold.

The product formed by this process may be removed from the mold, or alternatively remain in the mold where the product and the mold are used for various applications. The product may be a polymeric material, in which case the solution includes either monomers or polymers or both.

The product may have a wall morphology that includes a porous structure, a gel structure or overlapping regions of porous/gel structure. The polymeric product may have a wall morphology that includes a predominantly gel morphology with porous channels running from a periphery to a lumenal side, resulting in spotting on an outer wall surface.

The polymeric product may be a multi-layered product produced by repeating steps a), b) and c), at least once to produce a multi-layered product.

The polymeric product may be used as a reservoir for the delivery of drugs, therapeutics, cells, cell products, genes, viral vectors, proteins, peptides, hormones, carbohydrates, growth factors.

The polymeric product may contain microspheres containing preselected constituents, and wherein the product includes said microspheres distributed either uniformly or in a gradient within the wall structure of the product.

BRIEF DESCRIPTION OF DRAWINGS

The following is a description, by way of example only, of the method of producing tubes in accordance with the present invention, reference being had to the accompanying drawings, in which:

FIG. 1a is a cross section of a cylindrical mold used to manufacture tubes according to the present invention;

FIG. 1b is a cross section of an alternative embodiment of a cylindrical mold;

FIG. 1c is a cross section of another alternative embodiment of a cylindrical mold;

FIG. 1d is a cross section of another alternative embodiment of a cylindrical mold;

FIG. 3a shows the puncturing needle (D) is used to allow exit of air from the mold, while a syringe filled with solution (E) is injected through a needle (C) that punctures the lower injection port; FIG. 3b shows the filling of the mold with the liquid solution, air exits needle (D) as the solution fills the mold, and FIG. 3c shows the mold completely filled with solution with the visible air all displaced;

FIG. 8a shows a porous plug (L) is included within the mold of FIG. 5a prior to the injection of a liquid mixture; after phase separation and gelation, the outer surface of the porous material is coated with a phase-separated mixture without any affect on the inner porosity;

FIG. 8b shows a SEM micrograph of a coating applied to a porous poly(lactic-co-glycoloic acid [75:25] material that was included within the mold of FIG. 8a prior to phase separation produced with the mixture formulation of 7% HEMA, 93% water, 0.05% APS, 0.04% SMBS, 4000 rpm (also listed in Table 1 as example 3).

FIG. 12a is an optical micrograph of a cross-section of the wall of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12b shows an ESEM micrograph of a cross-section of the wall of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12c shows an optical micrograph of the outer longitudinal view of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12d shows an optical micrograph of the outer longitudinal view of a mixed porous/gel-like tube with no radial pores made in a silane-treated glass mold with the mixture formulation of 27% HEMA, 3% MMA, 70% water, 0.15% APS, 0.12% SMBS, 2700 rpm (also listed in Table 1 as example 10). The hollow structure was synthesized with the same formulation as in 12(a–c), but spun in a silane-treated glass mold;

FIG. 17b shows a SEM micrograph of cell-like surface patterns on the inner surface of a tube shown in FIG. 17a;

DETAILED DESCRIPTION OF THE INVENTION

Figure 2A:
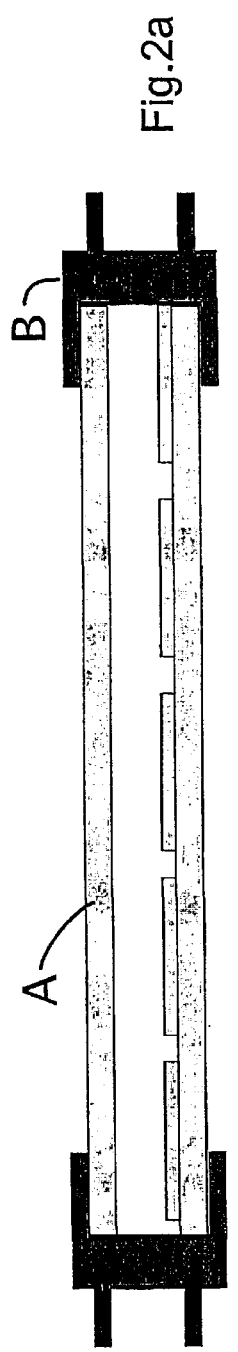
FIG. 2a is a cross section of an embodiment of a cylindrical mold with surface features along the length of the interior surface of the mold.

The forces that generate the tubular structures in this novel process are inertial forces associated with spinning a mold. A mold is filled with a homogeneous solution containing at least two components that can be phase separated thereby displacing substantially all of the visible air inside the mold. The mold is then rotated at some pre-determined speed, for example by being inserted into a rotating device, such as a drill chuck, or lathe. Phase separation of this homogeneous solution is induced by a phase separating agent while the mold is spinning.

The spinning will only send one of the phases to the inner surface of the mold, therefore broadly speaking this phase which adopts the shape of the inner surface of the mold needs to be stabilized to produce the product. Specifically, this separated phase must be stabilized to prevent it from falling off the surface of the mold and returning to the solution and generally the method of stabilization will depend on the nature of the material in the separated phase.

When the products are polymeric, the components of the solution may contain monomers or polymers or both. The phase separation process may result from changes in solubility as induced by changes in polymer chain length, changes in temperature, creation of a chemical product within the mold, changes in pH, or exposure to light, electric or magnetic fields. The greater density of one of the phase-separated phases results in the phase adopting the shape of the inner surface of the mold.

Gelation of the separated phase fixes the morphology of the formed product and the solvent phase remains in the center of the mold. For certain types of materials, gelation of the deposited phase-separated phase can be achieved using a number of methods, including but not restricted to, continued polymerization in the separated phase (where the deposited phase comprise monomers), cooling or heating of the mold, creation of a chemical reaction product within the mold, changing the pH of the phase-separated mixture and shining a frequency of the ultra-violet/visible light at the phase-separated mixture. By controlling rotational speed, formulation chemistry, surface chemistry and dimensions of the mold, the resulting morphology, mechanical and porosity properties, of the resulting product can be manipulated.

Tubes made using the invention were synthesized in custom-built disposable molds, are shown in FIGS. 1a to 4c. Referring to FIG. 1a, the mold, which may be a glass tubing A with an inside diameter (ID) between 0.02 and 100 mm, was cut to a desired length in the order of tens of centimeters. A septum B, currently made of rubber, was slipped over each end of the glass tube to serve as an injection port. Referring to FIGS. 3a to 3c, the tubing A is filled using a needle D pushed through the upper injection port to permit the exit of air during liquid injection. The desired homogeneous liquid was injected via needle C through septum B at the lower end of the mold, displacing all of the air within the mold. Withdrawing the needles D, then C, results in a seated, liquid filled mold. For concentricity and a uniform tube along the length, the sealed mold was placed into the chuck of a drill that had been mounted horizontally, using a spirit level.

FIGS. 1b, 1c and 1d show alternative embodiments of differently shaped molds that may be used to produce differently shaped tubes. For example, FIG. 1d shows a mold with multiple variations in diameter along the length of the mold used to manufacture tubes with the same shape.

Figure 2B:
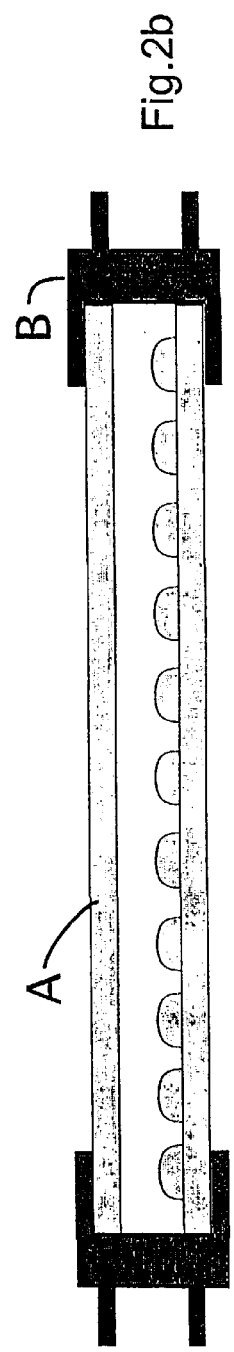
FIG. 2b is a cross section of an alternative embodiment of a cylindrical mold with surface features along the length of the interior surface of the mold.
Figure 2C:
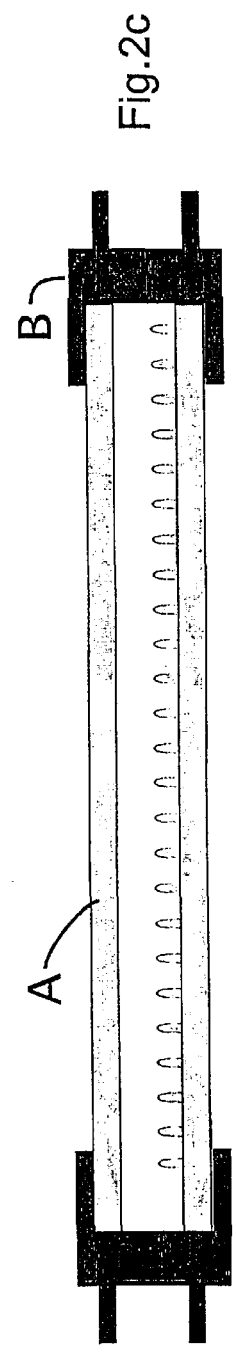
FIG. 2c is a cross section of another alternative embodiment of a cylindrical mold with surface features along the length of the interior surface of the mold.
Figure 2D:
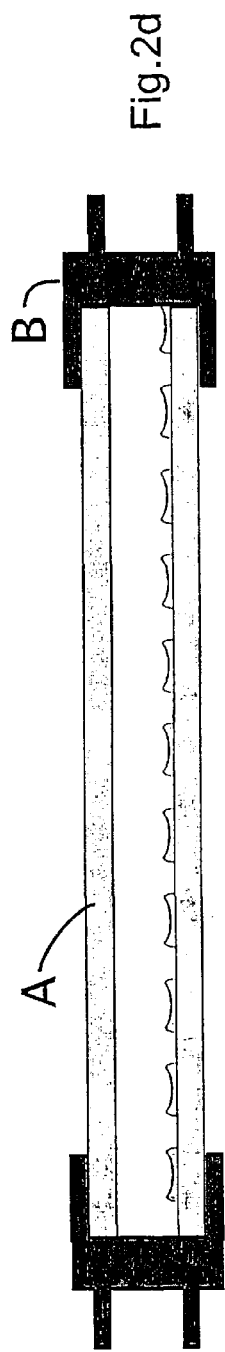
FIG. 2d is a cross section of another alternative embodiment of a cylindrical mold with surface features along the length of the interior surface of the mold.
Figures 3A, 3B, 3C:
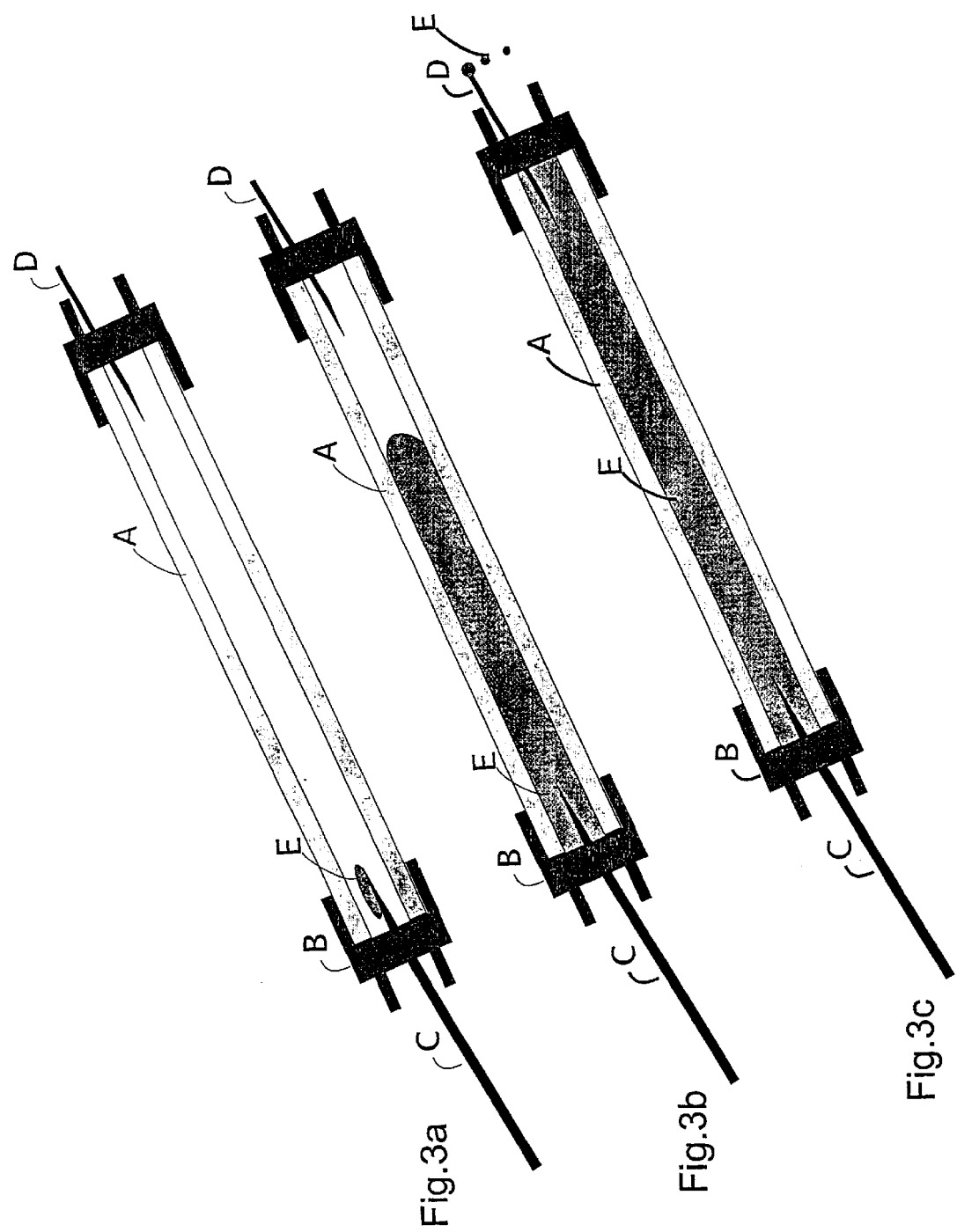
FIGS. 3a to 3c shows the steps of filling a cylindrical mold with a liquid.

FIG. 2a shows a cylindrical mold containing inner surface features such as rectangular fins on the inner surface used to manufacture tubes with rectangular indentations in the outer wall of the tubes. FIG. 2b shows a cylindrical mold containing inner surface features such as convex spherical lumps on the inner surface used to manufacture tubes with concave spherical indentations in the outer wall. FIG. 2c shows a cylindrical mold containing inner surface features such as pointed dimples on the inner surface used to manufacture tubes with dimples in the outer wall of the tube. FIG. 2d shows a cylindrical mold containing inner surface features such as concave spherical lumps on the inner surface used to manufacture tubes with these features embedded in the wall of the resulting tubes. In all these embodiments the surface features can be of symmetrical or non-symmetrical order, and different surface features can be used in any combination.

The inner surface of the mold can be modified using a surface treatment, physical or chemical, that affects the morphology of the wall of the hollow structure. For example, as the separated phase can be liquid-like in nature, it can be induced to bead, and form droplets on the inner surface, thereby influencing the wall morphology. Similarly, the desired surface treatment can allow the separated phase to spread across the inner surface, also influencing the wall morphology.

Figure 4A:
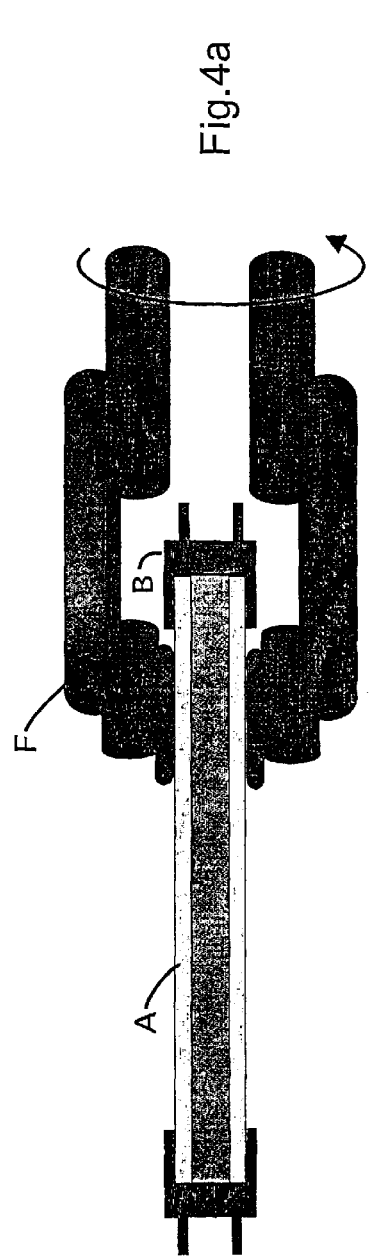
FIG. 4a shows a method of rotating the cylindrical mold in which the filled mold (A) is inserted into a drill chuck (F) and rotation of the mold is commenced.
Figure 4B:
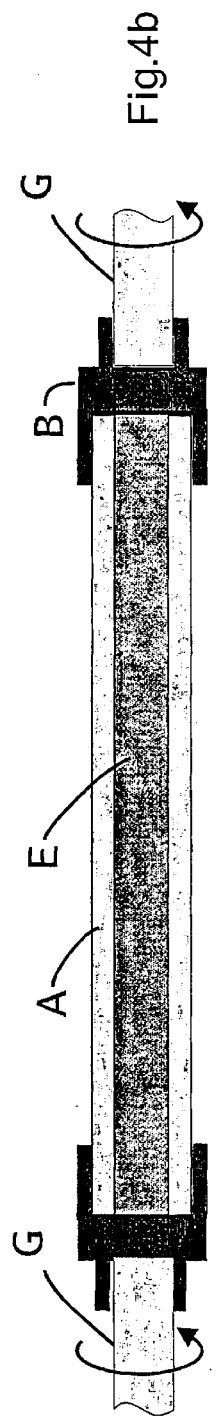
FIG. 4b shows another method of rotating the cylindrical mold in which the filled mold (A) is attached to the two ends of a lathe (G) and rotation of the mold is commenced.
Figure 4C:
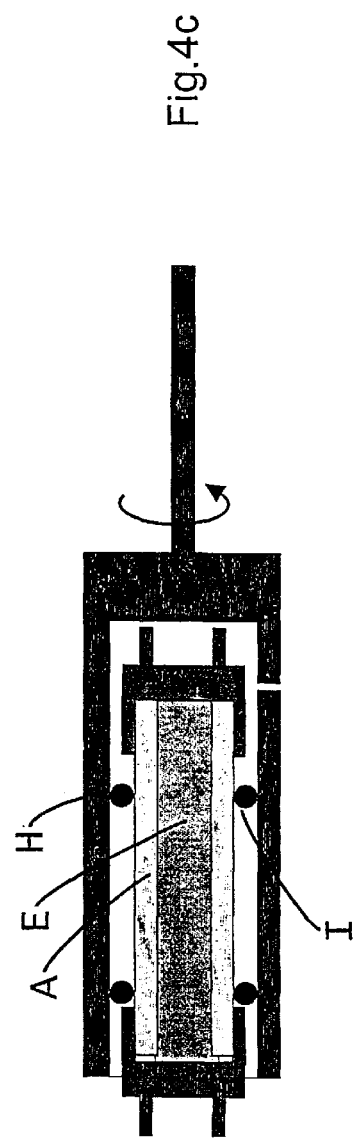
FIG. 4c shows another method of rotating the cylindrical mold in which the filled mold (A) is inserted into an adapter (H) so it can be placed into a drill chuck (F) and rotation of the mold is commenced and wherein O-rings (I) maintain position of mold (A) inside the adapter (H)

FIGS. 4a, 4b and 4c show various schemes for rotation of the filled mold (A). In FIG. 4a the mold A is inserted into a drill chuck (F) and rotation of mold is commenced. In FIG. 4b the filled mold (A) is attached to the two ends of a lathe (G) and rotation of mold is commenced. In FIG. 4c the filled mold (A) is inserted into an adapter (H) so it can be placed into a drill chuck (F) and rotation of mold is commenced. O-rings (I) maintain position of mold (A) inside the adapter (H).

Figure 5A:
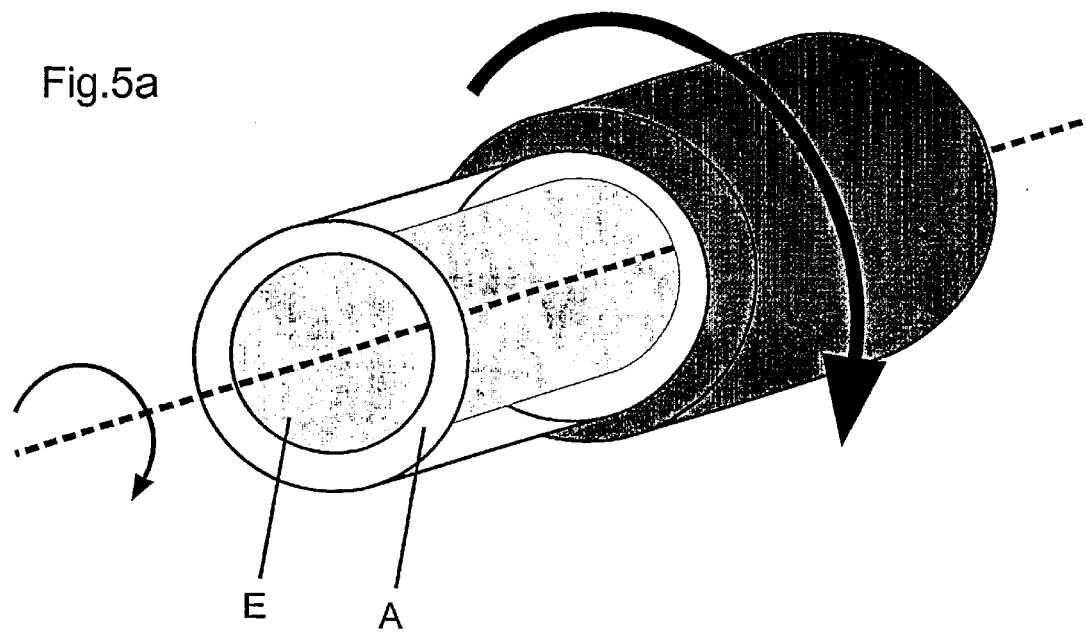
FIG. 5a is a perspective view showing a mold (A) filled with a liquid mixture (E) rotated about an axis at a suitable speed to centrifuge the phase that will eventually separate.
Figure 5B:
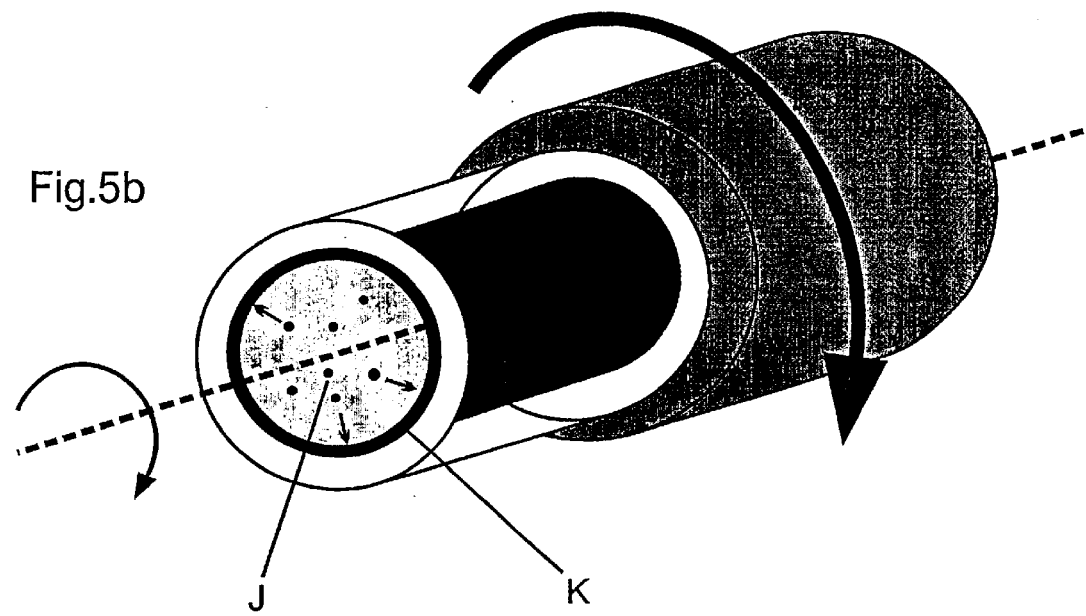
FIG. 5b shows the mixture (E) of FIG. 5a beginning to phase-separate during rotation, the dense phase (J) is centrifuged to the periphery of the mold where it adopts the shape of the inner surface of the mold (K)

FIGS. 5a and 5b show the process of phase separation during rotation of the mold. In FIG. 5a the mold (A) filled with a homogeneous mixture (E) is rotated about an axis at a suitable speed to centrifuge the phase that will eventually separate. FIG. 5b shows the mixture beginning to phase-separate during rotation. The dense phase (J) is centrifuged to the periphery of the mold where it adopts the shape of the mold (K).

It will be understood by those skilled in the art that the present method is not restricted to cylindrical molds or producing tubes therefrom. Any hollow structure may be used as a mold as long as it can be rotated about some axis to utilize centrifugal forces.

With the rotating mold containing the homogeneous liquid, phase separation of the mixture was induced, creating at least two phases from the liquid inside the mold. Phase separation may result in either liquid-liquid or viscoelastic solid-liquid interfaces or both within the mold. Phase separation can be induced using a range of different techniques and environmental changes. The addition of a propagating radical to a homogeneous monomer solution can induce phase separation, as can changes in temperature, pH, exposure of the mold to light, electric and magnetic fields.

After inducing different phases within the homogeneous solution, one or more of the phases will be forced to the periphery if the densities of the phases are different. The phase-separated particles then gel together, through covalent or physical bonding, to form a three-dimensional network between the separated phase(s). The gelation of particles must commence at a finite time after the onset of phase separation within the process of the invention.

A porous material can have an outer coating applied to it using this technology. Prior to the injection of a homogeneous mixture into the mold, a plug of porous material is inserted into the mold (FIG. 8a). After insertion of the porous structure into the mold, a homogeneous mixture is injected into the mold and rotated at the desired speed. The phase-separated phase is centrifuged through the pores of the inserted plug, and forms a structure on the outer surface of the porous plug, therefore sealing the material, without blocking the internal pores.

In a preferred embodiment of the present invention the homogenous solution includes at least two or more phases, one being a monomer, or polymer, and the other a solvent.

For homogeneous solutions containing monomer to be initiated, the initiation agent may be free radical initiators, thermal initiators and redox initiators. Examples of initiators includes ammonium persulfate or potassium persulfate with sodium metabisulfite, or tetramethylethylene diamine or ascorbic acid, azonitriles and derivatives thereof, alkyl peroxides and derivatives thereof, acyl peroxides and derivatives thereof, hydroperoxides and derivatives thereof; ketone peroxides and derivatives thereof, peresters and derivatives thereof and peroxy carbonates and derivatives thereof.

The homogeneous solution could also include a cross-linking agent depending on the structure of the final product that is desired and the polymer material that is formed. The crosslinking agent may be a multifunctional molecule with at least two reactive functionalities and includes multi-functional methacrylates or multi-functional acrylates, multi-functional acrylamides or multi-functional methacrylamides, or multi-functional star polymers of poly-ethylene glycol and preferably, but not limited to, one of ethylene glycol dimethacrylate (EDMA), hexamethylene dimethacrylate (HDMA), poly(ethylene glycol) dimethacrylate, 1,5-hexadiene-3,4-diol (DVG), 2,3-dihydroxybutanediol 1,4-dimethacrylate (BHDMA), 1,4-butanediol dimethacrylate (BDMA), 1,5-hexadiene (HD), methylene bisacrylamide (MBAm) multi-functional star polymers of poly(ethylene oxide) or combinations thereof.

An exemplary, non-limiting list of monomers that may be in the homogeneous mixture includes any one of acrylates, methacrylates, and derivatives thereof such as, but not limited to, 2-hydroxyethyl methacrylate, methyl methacrylate, 2-polyethylene glycol ethyl methacrylate, ethyl acrylate, 2-hydroxyethyl acrylate, acrylic acid, methacrylic acid, 2-chloroethyl methacrylate, butyl methacrylate, glycidyl methacrylate, hydroxypropyl methacrylate; acrylamides and derivatives thereof such as, but not limited to, methacrylamide, hydroxypropyl methacrylamide, N,N-diethyl acrylamide, N,N-dimethyl acrylamide, 2-chloroethyl acrylamide, 2-nitrobutyl acrylamide, N-vinyl pyrrolidone, acenaphthalene, N-vinyl acetamide, phenyl-acetylene, acrolein, methyl acrolein, N-vinyl pyridine, vinyl acetate, vinyl chloride, vinyl fluoride, vinyl methyl ketone, vinylidene chloride, styrene and derivatives thereof, propene, acrylonitrile, methacrylonitrile, acryloyl chloride, allyl acetate, allyl chloride, allylbenzene, butadiene and derivatives thereof, N-vinyl caprolactam, N-vinyl carbazole, cinnamates and derivatives thereof, citraconimide and derivatives thereof, crotonic acid, diallyl phthalate, ethylene and derivatives thereof such as, but not limited to 1,1 diphenyl-ethylene, chlorotrifluoro-ethylene, dichloroethylene, tetrachloro-ethylene; fumarates and derivatives thereof, hexene and derivatives thereof, isoprene and derivatives thereof such as, but not limited to isopropenyl acetate, isopropenyl methyl ketone, isopropenylisocyanate; itaconate and derivatives thereof, itaconamide and derivatives thereof; diethyl maleate, 2-(acryloyloxy)ethyl diethyl phosphate, vinyl phosphonates and derivatives thereof, maleic anhydride, maleimide, silicone polymers, and derivatives thereof; and any combination thereof.

An exemplary, non-limiting list of polymers that may be in the homogeneous mixture includes any of polyacrylates, polysulfone, peptide sequences, proteins, oligopeptides, collagen, fibronectin, laminin, polymethacrylates such as but not limited to poly(methyl methacrylate), poly(ethoxyethyl methacrylate), poly(hydroxyethylmethacrylate; polyvinyl acetates polyacetates, polyesters, polyamides, polycarbonates, polyanhydrides, polyamino acids, such as but not limited to poly(N-vinyl pyrrolidinone), poly(vinyl acetate), poly(vinyl alcohol, poly(hydroxypropyl methacrylamide), poly(caprolactone), poly(dioxanone) polyglycolic acid, polylactic acid, copolymers of lactic and glycolic acids, and polytrimethylene carbonates, poly (butadiene), polystyrene, polyacrylonitrile, poly (chloroprene), neoprene, poly(isobutene), poly(isoprene), polypropylene, polytetrafluoroethylene, poly(vinylidene fluoride), poly(chlorotrifluoroethylene), poly(vinyl chloride), poly(oxymethylene), poly(ethylene terephthalate), poly(oxyethylene) poly(oxyterephthaloyl), polyamides such as but not limited to, poly[imino(1-oxohexamethylene)], poly(iminoadipoyl-iminohexamethalene), poly(iminohexamethylene-iminosebacoyl), poly[imino(1-oxododecamethylene)], cellulose, polysulfones, hyalonic acid, sodium hyaluronate, alginate, agarose, chitosan, chitin, and mixtures thereof.

A non-limiting exemplary list of solvents in the homogeneous mixture for the monomer and/or polymers includes any neucleophilic or electrophilic molecule including, but not necessarily restricted to water, alcohols, ethylene glycol, ethanol, acetone, poly(ethylene glycol), dimethyl sulfoxide, dimethyl formamide, alkanes and derivatives thereof, acetonitrile, acetic acid, benzene, acetic anhydride, benzyl acetate, carbon tetrachloride, chlorobenzene, n-butanol, 2-chloroethanol, chloroform, cyclohexane, cyclohexanol, dichloromethane, diethyl ether, di(ethylene glycol), di(ethylene glycol) monomethyl ether, 1,4 dioxane, N,N, dimethyl acetamide, N,N,dimethyl formamide, ethyl acetate, formaldehyde, n-heptane, hexachloroethane, hexane, isobutanol, isopropanol, methanol, methyl ethyl ketone, nitrobenzene, n-octane, n-pentanol, propyl acetate, propylene glycol, pyridene, tetrahydrofuran, toluene, trichloroethylene, o-xylene and p-xylene, or aforementioned monomers or crosslinking agents, or mixtures thereof.

The solvent can be chosen to solubilize the monomer but not a polymer or crosslinked polymer formed from the monomer. One of the components may include a polymer dissolved in a solvent.

In another embodiment a tapered hollow structure with changing dimensions along it length can be manufactured where the sealed mold is rotated at a predetermined angle between 0 and 90° from the horizontal plane.

In another embodiment controlling the viscoelastic properties of the separated phase and/or the rotation speed can create cell-invasive hollow structures. If the separated phase has substantial elastic properties, they will not coalesce, and after gelation, the porous network between the phase is large enough for the penetration of cells into the construct.

In another embodiment multi-layered structures can be formed by repeating the process as many times as desired. After forming the first layer, the solvent phase can be removed and another homogeneous mixture injected into the mold. The first layer coating the mold, effectively becomes the mold for the next coating and the second formation penetrates into the first coating, binding them together after gelation. The multi-layered hollow structures can be manufactured using any or all of the types of tubes described in the examples, made from any material, similar or different materials, in any order required, as many times as required. A layered wall structure (ie. gel-like and porous) can be made by multiple formulations and multiple rotations or in one formulation/one rotation.

Manufacture of both physically and chemically crosslinked tubes are possible using this technique, as is the manufacture of both degradable and non-degradable polymer tubes. Those skilled in the art will appreciate the many applications for which the structures produced with the present method may be used. The ability to control the morphology, porosity and wall thickness of these tubes permits their use as drug delivery vehicles, when the structures are composed of physiologically acceptable materials. Drugs can also be incorporated in other materials that are incorporated into the tube, or in the tube wall itself. For example, the tube can be filled with a material, such as, but not limited to, a hydrogel, in which drugs are dispersed. Alternatively, the wall structure can serve as a reservoir for the drug, which may be incorporated in another material/drug reservoir, such as microspheres releasing the drug. The drug may be delivered uniformly or in a gradient. By tuning the set-up, a gradient can be established. The drug may include, but is not limited to, proteins, peptides, genes, vectors, growth factors, hormones, oligonucleotides, cell products, or cells or combinations thereof.

It is also possible to produce hollow structures that allow molecules to diffuse across the wall structure. Also hollow structures can be produced that selectively allow the diffusion of molecules based on size and/or shape to diffuse across the wall structure and to allow preferential directional drug delivery. The invention can also provide tubular structures with the appropriate mechanical properties for their end use—for example to match the mechanical properties of the tissue in which they are to be implanted.

The present method can be used to produce tubular structures that have an outer gel phase and an inner porous phase. The present method can also be used to provide a tubular structure with overlapping regions of porous phase/gel phase.

A significant advantage of the present method can be used to make hollow structures of various dimensions with internal diameters from 10 $\mu$m to 100 cm.

The present invention will now be illustrated with several non-limiting examples. The first examples relate to 2-hydroxyethyl methacrylate polymers and copolymers that are synthesized (and crosslinked) in a rotating mold where phase separation precedes gelation of polymer networks formed, resulting in a tube due to centrifugal forces. Such morphologies given as examples of 2-hydroxyethyl methacrylate and its copolymers are also relevant to any monomeric or polymeric system that can be induced to phase separate in a liquid-filled rotating mold.

EXAMPLE 1

2-hydroxyethyl methacrylate (HEMA) was polymerized in the presence of excess water, with a crosslinking agent, preferably, but not limited to ethylene dimethacrylate (EDMA), using a free radical initiating system and preferably an ammonium persulfate (APS)/sodium metabisulfite (SMBS) redox initiating system. A homogeneous mixture, with components detailed in Table 1, was injected into a cylindrical glass mold as described for the process involving 2-hydroxyethyl methacrylate. The homogeneous mixture was made by adding the relevant quantities of HEMA, and water into a glass vial, and mixing in the glass vial. Mixing of the solution was repeated after the appropriate amount of 10% APS solution listed in Table 1 was added. The appropriate volume of 10% SMBS solution was added to this mixture, which was mixed for an additional 30 seconds. The homogeneous monomer mixture was then drawn into a Luer-lok syringe using a 20-gauge needle. The needle was removed from the syringe and, using a new 20-gauge needle and a 0.8 $\mu$m filter, the monomer mixture was injected into the polymerization molds.

Figure 6:
FIG. 6 shows an environmental scanning electron microscope (ESEM) micrograph of a gel-like coating on the inside of a glass mold, produced with the mixture formulation of 1% HEMA, 99% water, 0.01% APS, 0.01% SMBS, 4000 rpm (also listed in Table 1 as example 1)

The sealed mold was placed in the chuck of a RZR-1 dual range, variable speed stirring drill (Heidolph, Germany) that had been mounted horizontally, using a spirit level. The rotational speed was 2700 rpm as listed in Table 1. The resulting gel-like coating on the inner surface of the mold is shown in FIG. 6 and is approximately 10±3 μm thick. FIG. 6 shows an environmental scanning electron microscope (ESEM) micrograph of a gel-like coating on the inside of a glass mold, in which the mixture formulation was 1% HEMA, 99% water, 0.01% APS, 0.01% SMBS, 4000 rpm.

EXAMPLE 2

Figure 7B:
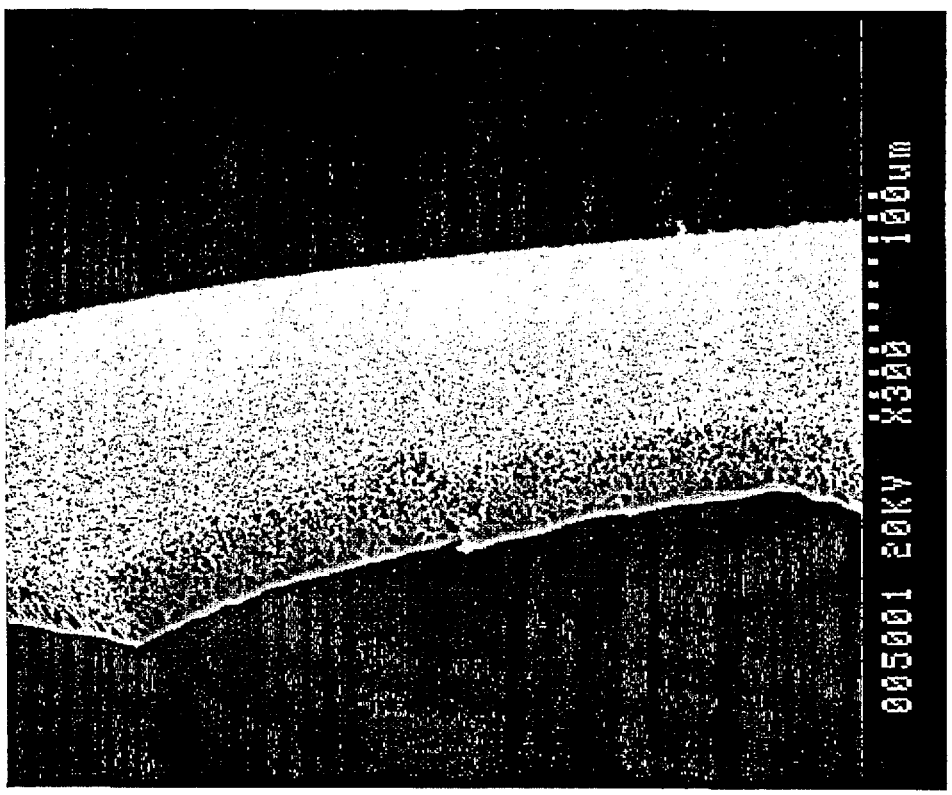
FIG. 7b shows a SEM micrograph of the inner surface of a porous coating applied to the inside of a glass mold, produced with the mixture formulation of 1.9% HEMA, 0.1% PEGMA, 98% water, 0.02% APS, 0.02% SMBS, 2700 rpm (also listed in Table 1 as example 2)
Figure 7A:
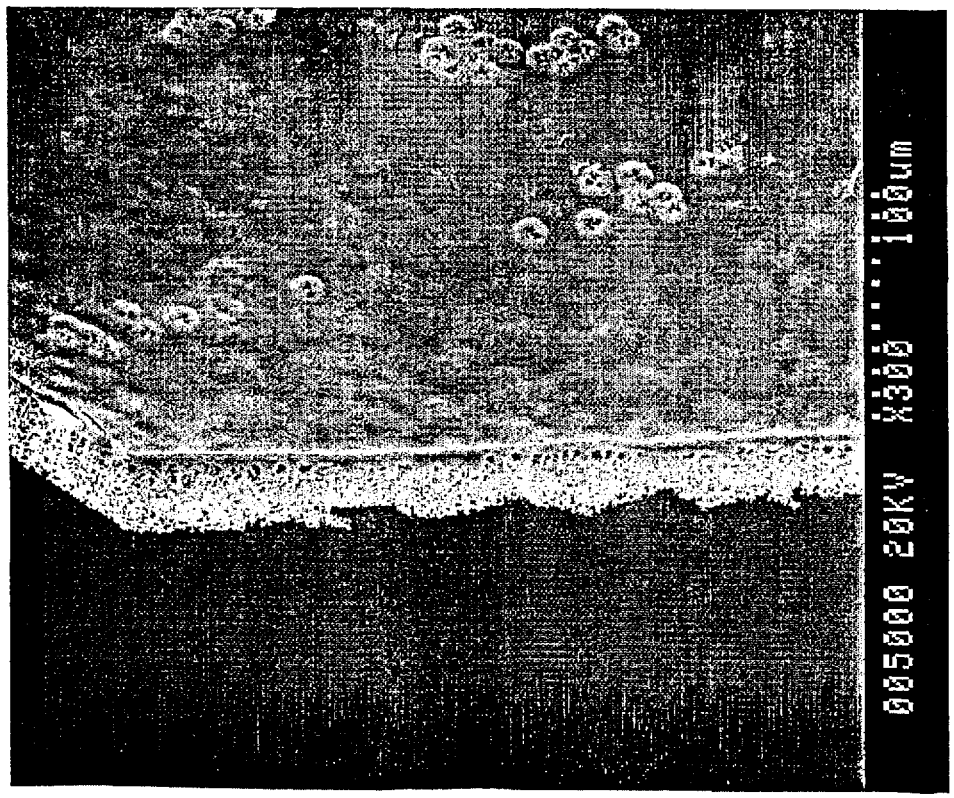
FIG. 7a shows a scanning electron microscope (SEM) micrograph of the outer surface of a porous coating applied to the inside of a glass mold, produced with the mixture formulation of 1.9% HEMA, 0.1% PEGMA, 98% water, 0.02% APS, 0.02% SMBS, 2700 rpm (also listed in Table 1 as example 2)

A coating with both gel-like and porous morphologies was prepared with the same methodology as Example 1; the monomer mixture used also included poly(ethylene glycol) methacrylate as a comonomer. The monomer mixture and rotation conditions used in Example 2 are listed in Table 1. The resulting porous material/gel-like hybrid coating on the inner surface of the mold is shown in FIGS. 7a and 7b with the outer gel-like coating (the surface that is against the inside of the mold) facing forward in FIG. 7a and the inner porous structure (the one against the water) facing forward in FIG. 7b. The thickness of the coating is approximately 30±5 μm thick. The micrograph in FIGS. 7a and 7b were taken after removing the coating from the glass mold. More specifically, FIG. 7a shows a scanning electron microscope (SEM) micrograph of the outer surface of a porous coating applied to the inside of a glass mold, in which the mixture is 1.9% HEMA, 0.1% PEGMA, 98% water, 0.02% APS, 0.02% SMBS, 2700 rpm. FIG. 7b shows the inner surface of a porous coating applied to the inside of a glass mold, in which the mixture formulation is 1.9% HEMA, 0.1% PEGMA, 98% water, 0.02% APS, 0.02% SMBS, 2700 rpm.

EXAMPLE 3

A porous material can have an outer coating applied to it using this technology. The coating that can be either gel-like or have porous morphology or both was prepared with similar methodology as in Example 1. Prior to the injection of a homogeneous mixture into the mold, a plug of porous material is inserted into the mold (FIG. 8a). Porous PLGA is manufactured using techniques previously described (Holy et al, Biomaterials, 20, 1177–1185, 1999), however the porous material may be made of any material, including polymers, ceramics, metals, composites, or combinations thereof. After insertion of the porous structure into the mold, the homogeneous mixture listed in Table 1 as Example 3 is injected into the mold and the mold rotated at the speed listed in Table 1. The resulting coated porous material removed from the mold is shown in FIG. 8b. There was no coating or blocked pores on the inside of the porous material; the only coating visible was on the outside. This example demonstrates the successful outer coating (and sealing) of a porous material without affecting the morphology of the said porous material.

EXAMPLE 4–5

Figure 9A:
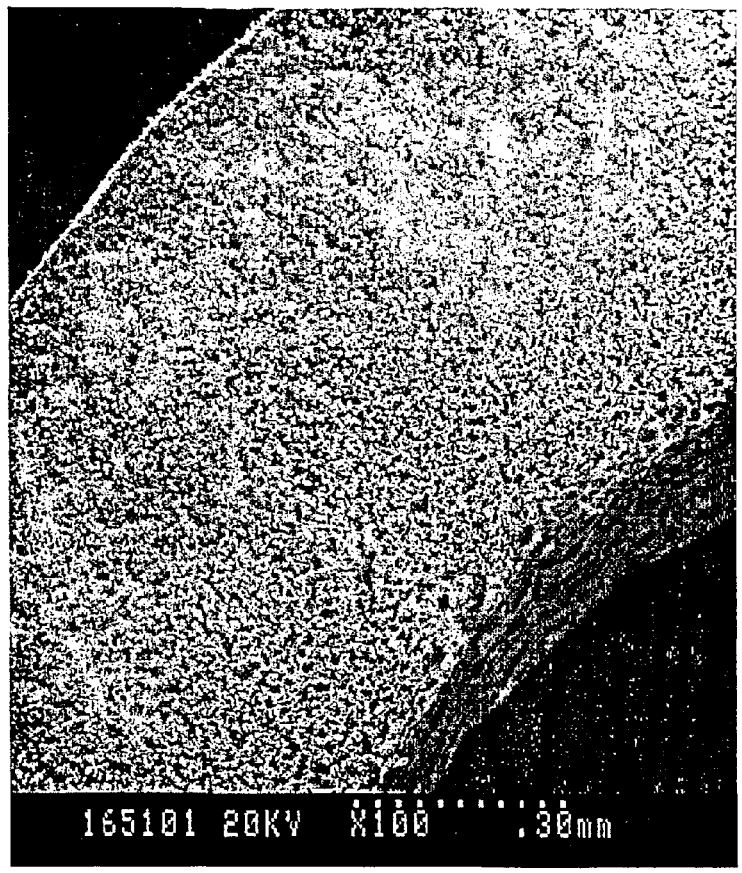
FIG. 9a shows a SEM micrograph of a cross-section of the wall of a cell-invasive, porous tube produced with the mixture formulation of 15.75% HEMA, 2.25% MMA, 82% water, 0.02% EDMA, 0.08% APS, 0.06% SMBS, 2700 rpm (also listed in Table 1 as example 4)
Figure 9B:
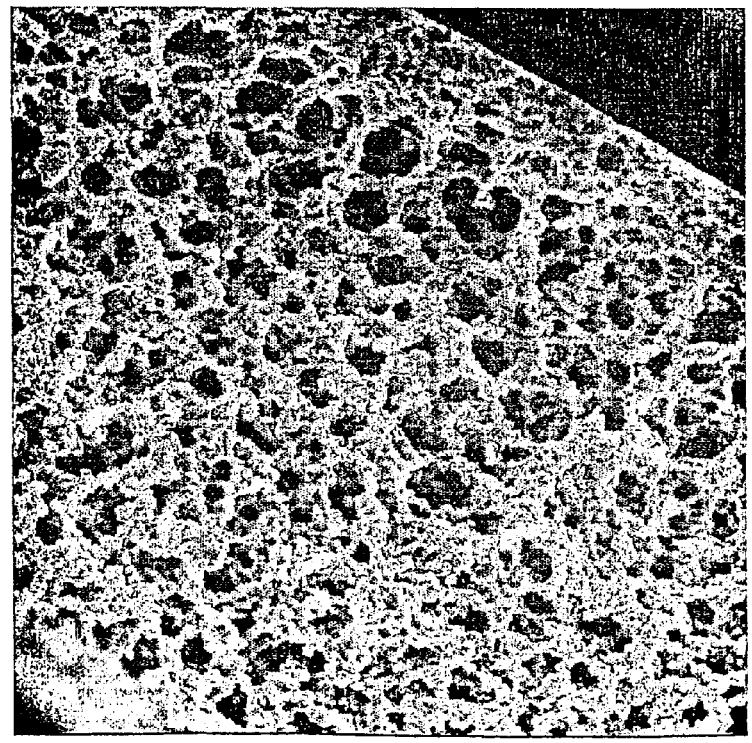
FIG. 9b is an ESEM micrograph of a cross-section of the wall of a cell-invasive, porous tube produced with the mixture formulation of 20% HEMA, 80% water, 0.02% EDMA, 0.1% APS, 0.04% TEMED, 2700 rpm (also listed in Table 1 as example 5)

A porous, cell-invasive tube can be manufactured with the same methodology as Example 1, except the monomer mixture used may include methyl methacrylate (MMA) as a comonomer. Example 5 also substitutes TEMED for SMBS as the second component in the initiating system. The monomer mixture and rotation conditions used in Examples 4–5 are listed in Table 1, and both result in cell invasive, porous tubes. In this particular instance, the use of a faster initiating system, such as, but not limited to the APS/TEMED redox system, or increased concentrations of initiator in the homogeneous mixture is beneficial to achieve the porous structure. FIGS. 9a and 9b show a porous wall morphology of Examples 4 and 5. Formation is due to sudden phase separation, in addition to viscoelastic particles separating, that do not coalesce.

EXAMPLES 6–7

A semi-porous, cell-impermeable tube can be manufactured with the same methodology as Example 1, except the monomer mixture used may include methyl methacrylate (MMA) as a comonomer. The monomer mixture and rotation conditions used in Examples 6–7 are listed in Table 1, and both result in semi-permeable non-cell invasive, tubes. In example 6, the rotation speed is at 10,000 rpm; the high rotation speed compacts the phase separating structure against the tube wall, resulting in gel-like wall morphology with closed cell pores that affect diffusion across the wall membrane (FIG. 10a).

Figure 10B:
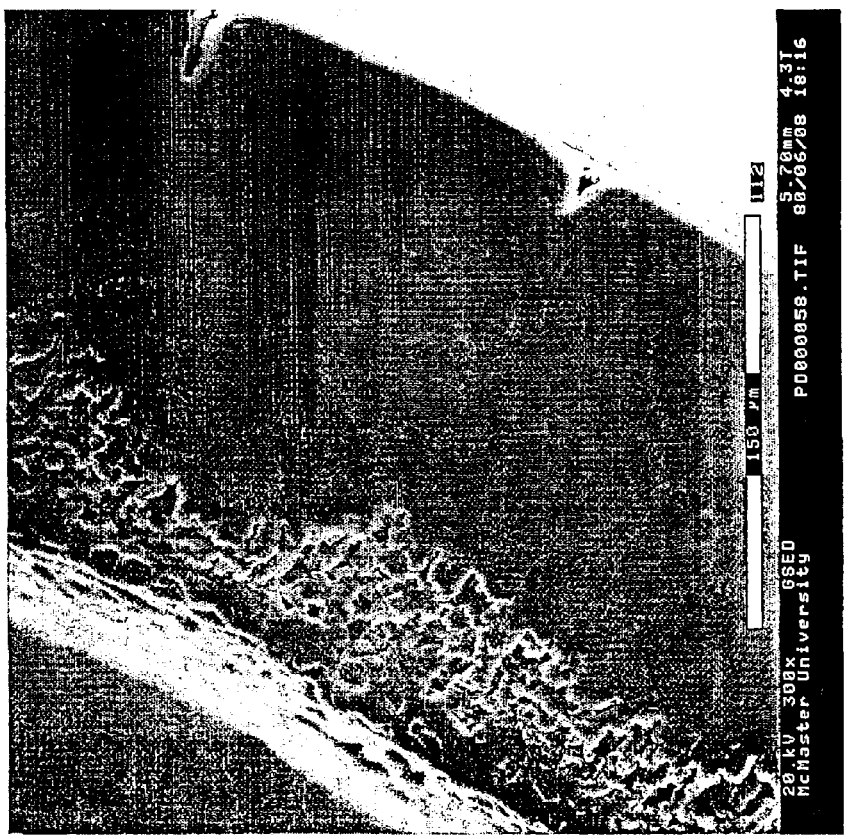
FIG. 10b shows an ESEM micrograph of a cross-section of the wall of a predominantly gel-like tube produced with the mixture formulation of 23.25% HEMA, 1.75% MMA, 75% water, 0.025% EDMA, 0.125% APS, 0.1% SMBS, 2500 rpm (also listed in Table 1 as example 7)
Figure 10A:
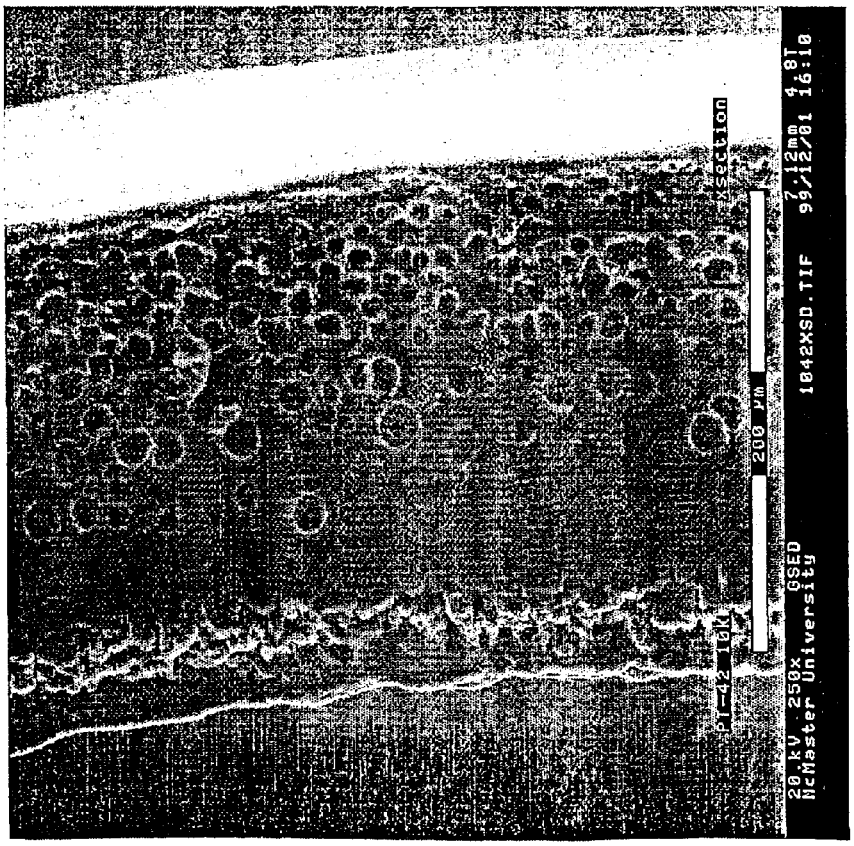
FIG. 10a shows an ESEM micrograph of a cross-section of the wall of a predominantly gel-like tube produced with the mixture formulation of 20% HEMA, 80% water, 0.02% EDMA, 0.1% APS, 0.06% SMBS, 10 000 rpm (also listed in Table 1 as example 6)

In the instance of example 7, the initiating system as a phase separating agent may be in a lower concentration, as slower phase separation is beneficial to achieve the non-porous, gel-like structure at lower rotation speeds (FIG. 10b).

EXAMPLES 8–9

A mixed porous/gel-like tube can be manufactured with the same methodology as Example 1, except the monomer mixture used may include MMA and/or ethylene glycol EG) which affects phase separation. The monomer mixture and rotation conditions used in Examples 8–9 are listed in Table 1, and both result in mixed porous and gel-like tubes manufactured with one polymerization. The bi-layer morphology of the cross-section of Example 8, seen in FIG. 11a, is due to the precipitation of a liquid-like phase at the start of the phase separation followed by a viscoelastic precipitate towards the end of the phase separation. Co-solvents other than water, such as EG, are therefore useful for delaying or accelerating phase separation, and therefore control the bi-layered morphology of the wall.

Figure 11B:
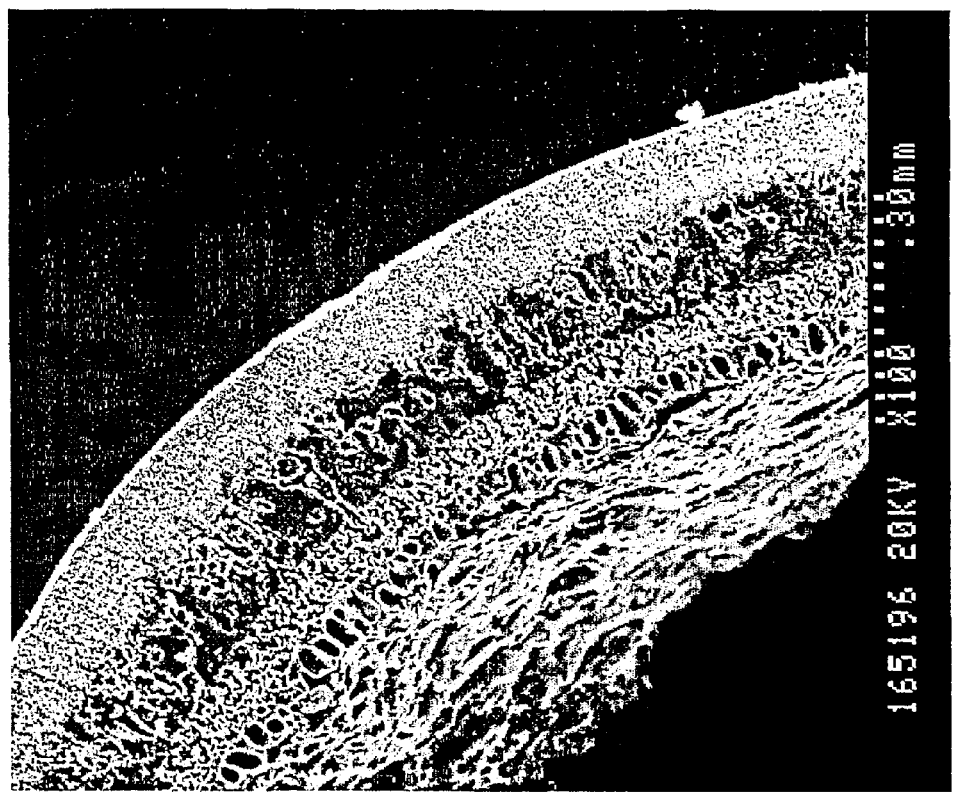
FIG. 11b is a SEM micrograph of a cross-section of the wall of a mixed porous/gel-like tube, produced with the mixture formulation of 27% HEMA, 3% MMA, 70% water, 0.1% APS, 0.075% SMBS, 4000 rpm (also listed in Table 1 as example 9)
Figure 11A:
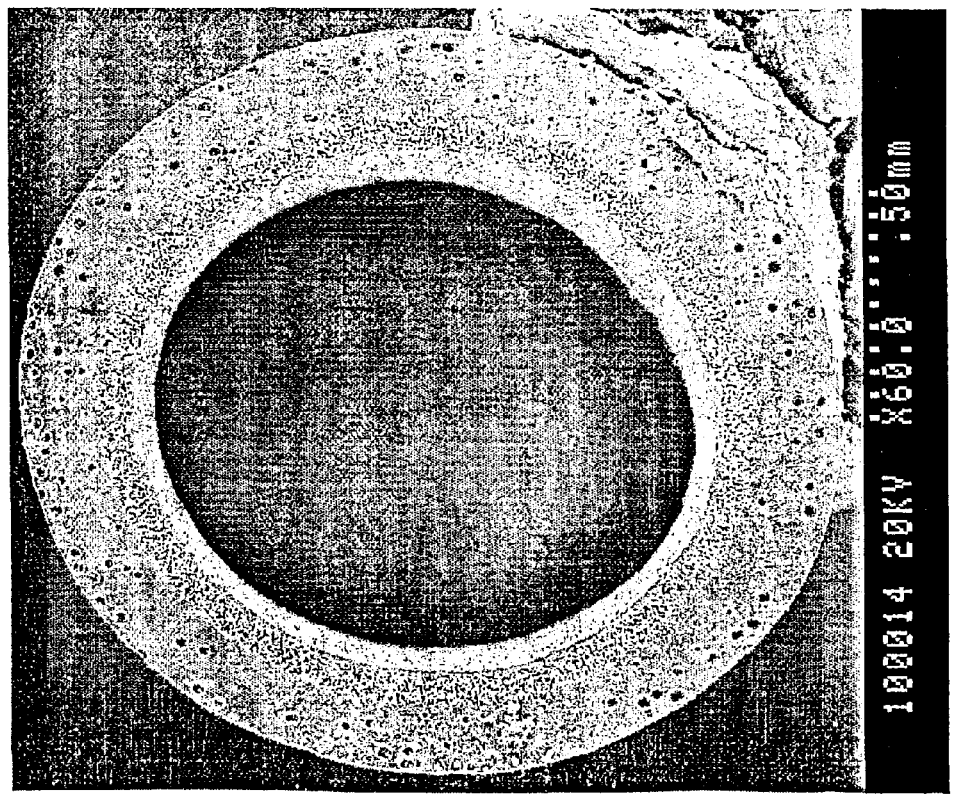
FIG. 11a shows an SEM micrograph of a cross-section of the wall of a mixed porous/gel-like tube produced with the mixture formulation of 28.3% HEMA, 58.3% water, 5.3% MMA, 8.3% ethylene glycol, 0.125% APS, 0.1% SMBS, 2700 rpm (also listed in Table 1 as example 8)

For Example 9, a porous/gel-like tube can be manufactured with the same methodology as Example 1, except faster speeds in combination with slower phase separation can induce the morphology in FIG. 11b.

EXAMPLE 10

A mixed porous/gel-like tube with radial porosity can be manufactured with the same methodology as Example 1, when the denser separating phase can be beaded as droplets on the inner surface of the rigid mold. The contact angle of the separating phase can be influenced by surface modification of the rigid mold, or changing the material of the inside of the mold. The wall morphology can therefore be influenced by the surface chemistry of the mold. The monomer mixture and rotation conditions used in Example 10 are listed in Table 1, may include co-solvents such as methyl methacrylate or ethylene glycol to influence the solubility of the separated phase. FIGS. 12a and 12b are micrographs of the porous/gel-like tube with radial porosity cross-section, with FIG. 12c showing the outer longitudinal morphology of the same formulation. The hollow structure shown in the optical micrograph in FIG. 12d was synthesized with the same formulation as Example 10, but was formed in a silane-treated glass mold. The silanating agent was Sigmacote from Sigma-Aldrich. The Sigmacote solution was drawn up into glass molds and then dried in an oven to evaporate the solvent. Contact angle studies on glass slides showed the water contact angle changed from 44.7±3°/11.6±1.8° to 47±0.3°/44±0.4° after surface modification. The glass mold was then used with the formulation listed as Example 10 in Table 1. The hollow fiber membranes had equilibrium water contents between 42% and 57%; elastic moduli between 22 kPa and 400 kPa, and diffusive permeabilities between $10^{-7}$ and $10^{-9}$ cm$^2$s$^{-1}$ for vitamin B12 and dextran 10 kD. Similar mechanical strengths of the tube walls could be achieved with significantly different permeabilities, reflecting their intrinsic microstructures. The beading described in Example 10 permits highly diffusive hollow structures while maintaining good mechanical strength.

EXAMPLE 11

Figure 13B:
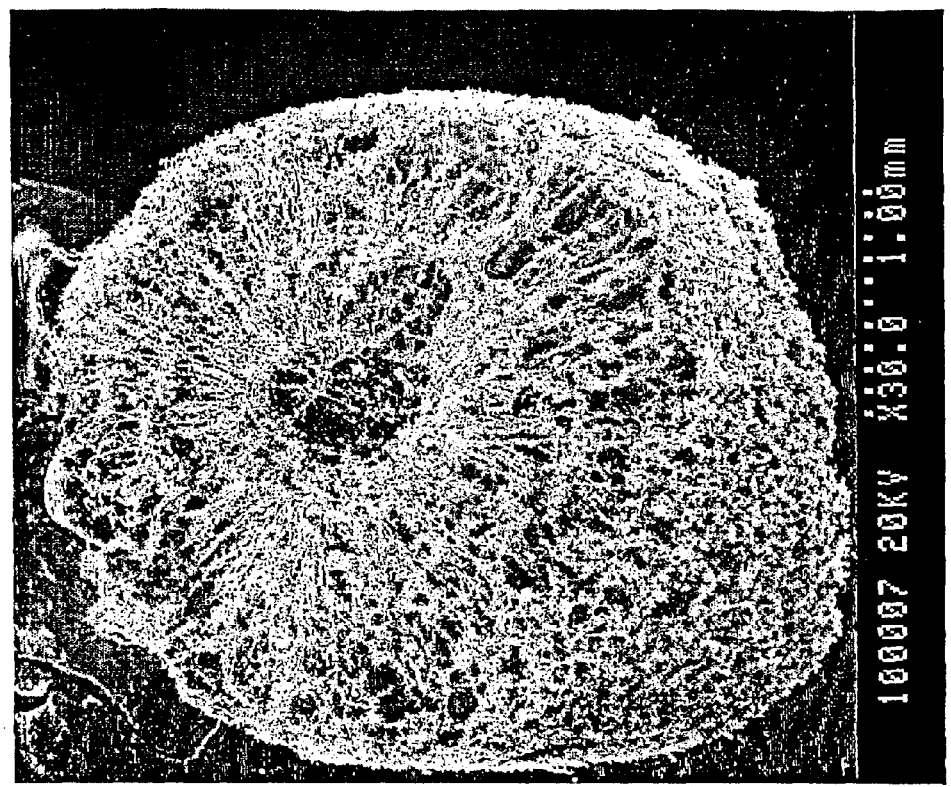
FIG. 13b shows a SEM micrograph of a cross-section of a predominantly porous wall with radial fibers produced with the mixture formulation of 2% HEMA, 98% water, 0.02% APS, 0.02% SMBS, 30 rpm (also listed in Table 1 as example 12)
Figure 13A:
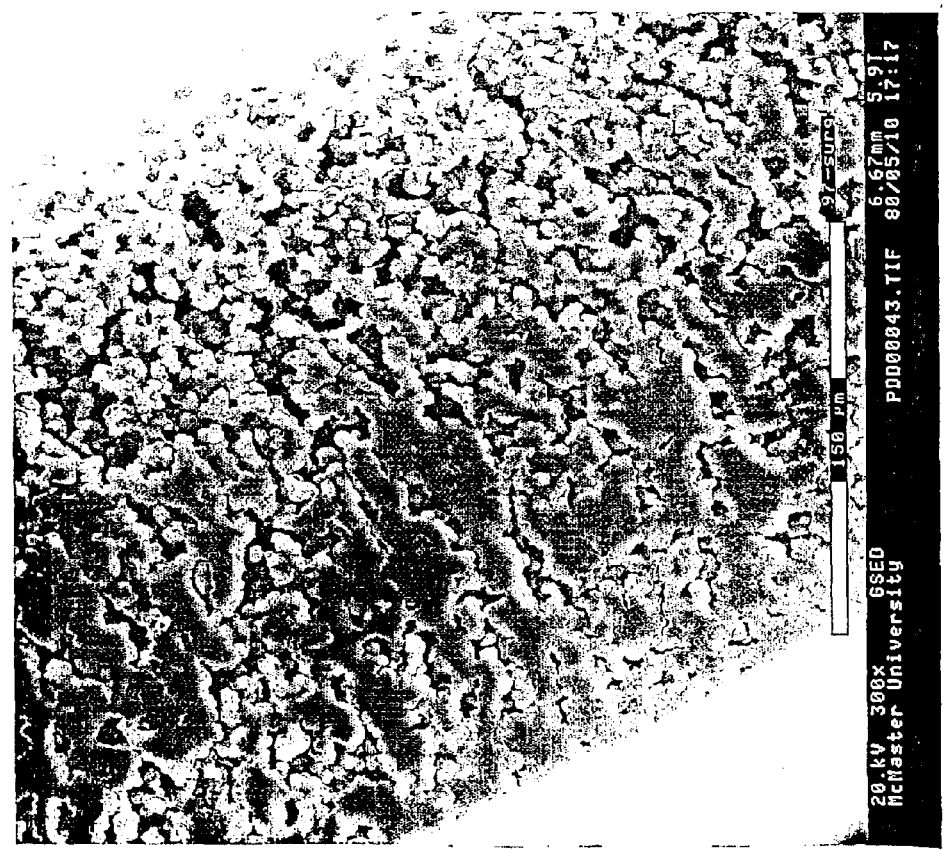
FIG. 13a shows an ESEM micrograph of a cross-section of a predominantly gel-like wall with radial pores produced with the mixture formulation of 20% HEMA, 80% water, 0.1% APS, 0.04% SMBS, 2700 rpm (also listed in Table 1 as example 11)

A porous tube with pores that are radial in nature can be manufactured with the same methodology as Example 1, with a monomer formulation mixture and rotation conditions listed in Table 1 as Example 11. The wall morphology is predominantly gel, with channels or pores that penetrate in a radial manner that does not require beading as in Example 10. An example of this morphology is shown in FIG. 13a.

EXAMPLE 12

A porous tube with fibers that are radial can be manufactured with the same methodology as Example 1, with a monomer formulation mixture and rotation conditions listed in Table 1 for Example 12. The wall morphology is predominantly space, with fibers that penetrate in a radial manner. The inner lumen of the formed hollow structure is small relative to the wall thickness and an example of this morphology is shown in FIG. 13b. In this example, the prevention of sedimentation of low concentrations was achieved with a slow rotation rate. This surprising result demonstrates the profound effect of rotation rate on the wall morphology, especially compared to Example 2 (FIGS. 7a and 7b) which has the similar monomer concentrations, but significantly different rotation rates.

EXAMPLE 13

Figure 14:
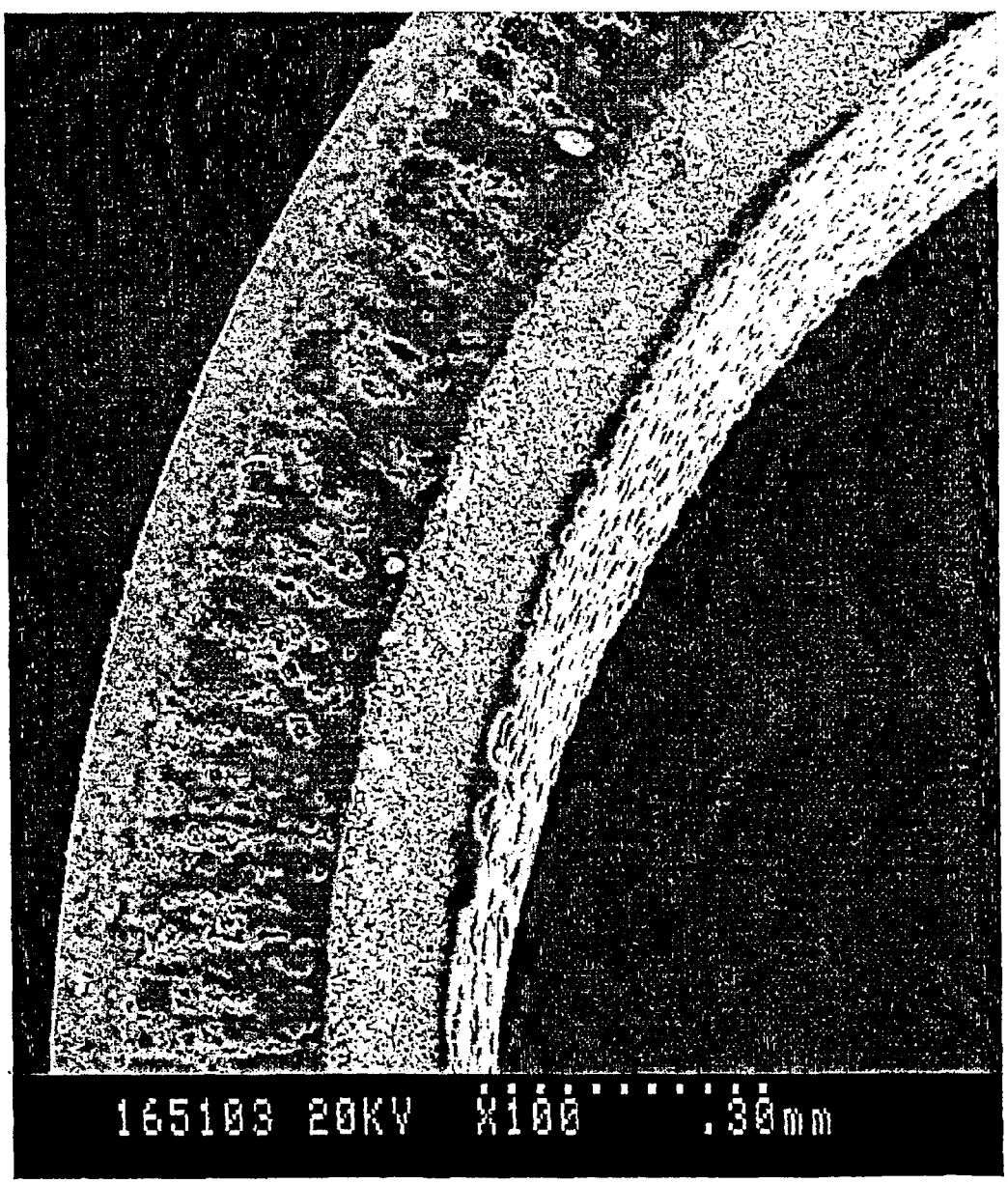
FIG. 14 shows a SEM micrograph of a cross-section of the wall of a multi-layered tube produced with the mixture formulation of ($1^{st}$ (outer) layer 1.8% HEMA, 0.2% PEGDMA, 98% water, 0.002% APS, 0.002% SMBS, 2700 rpm; $2^{nd}$ (inner) layer 27% HEMA, 3% MMA, 70% water, 0.12% APS, 0.09% SMBS, 4000 rpm.) (also listed in Table 1 as example 13)

Morphology of a cross-section of the wall of a multi-layered tube with the mixture formulation listed in Table 1 as example 13. These multi-layered tubes are can be manufactured with the same methodology as Example 1, repeated as many times as required. Example 13 in Table 1 refers to the first, outer, layer formed (o) and the second, inner formed layer (i). Multi-layered hollow structures are possible by forming one layer and using the formed hollow structure as the surface coating of the mold and the hollow structure process repeated as many times as desired. The multi-layered hollow structures can be manufactured using any or all of the types of tubes described in the examples, made from any material, similar or different materials, in any order required, as many times as required. An example is shown in FIG. 14.

EXAMPLE 14

Figure 15:
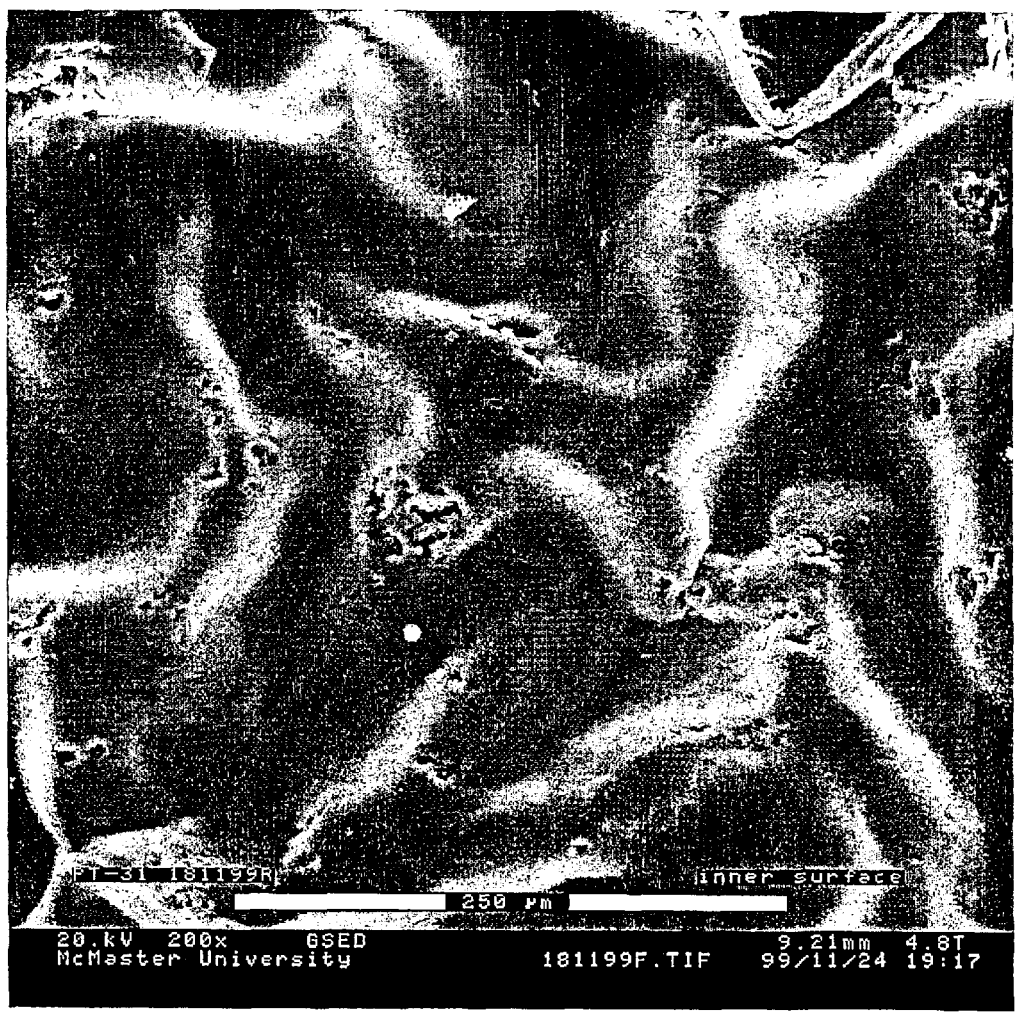
FIG. 15 shows an ESEM micrograph of the inner lumen of a tube with a smooth inner surface produced with the mixture formulation of 20% HEMA, 80% water, 0.02% EDMA, 0.1% APS, 0.04% SMBS, 2700 rpm (also listed in Table 1 as example 14)

Smooth surface morphology the inner layer of a tube with the mixture formulation listed in Table 1 as Example 14 can be manufactured with the same methodology as Example 1. A tube with a smooth inner surface is shown in FIG. 15.

EXAMPLE 15

Figure 16B:
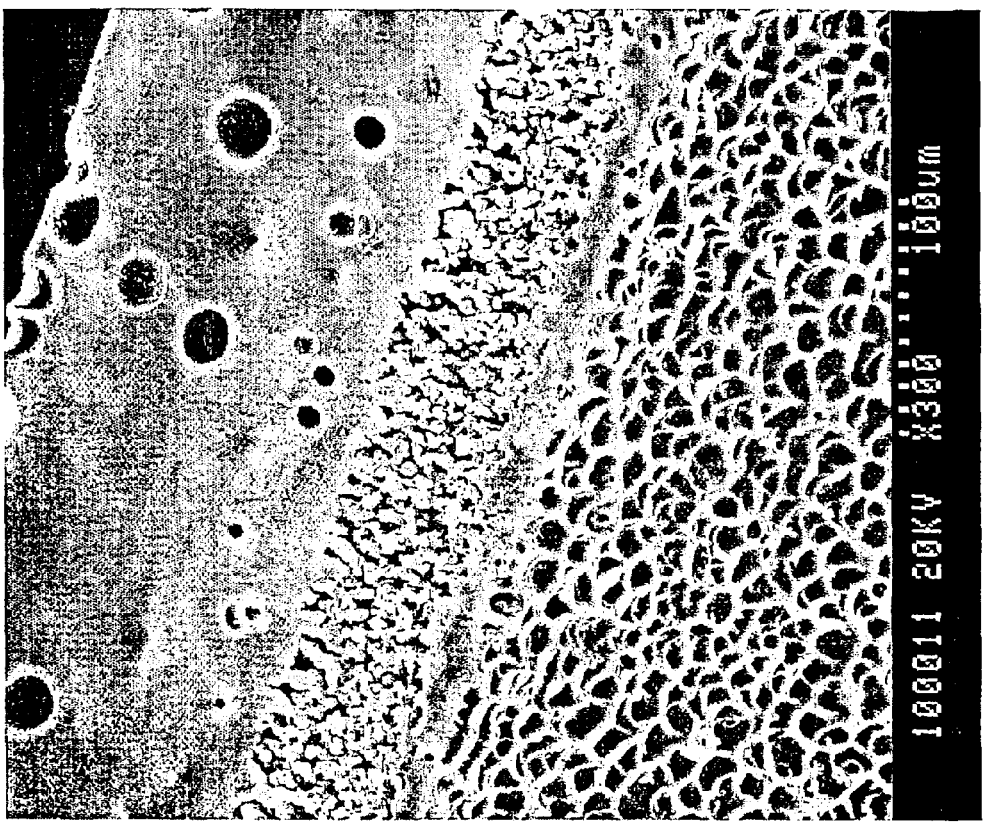
FIG. 16b shows a SEM micrograph of a lateral cross-section of the wall of the tube shown in FIG. 16a near the mold/polymer interface showing a gel-like/porous wall morphology and a dimpled/rough inner surface.
Figure 16A:
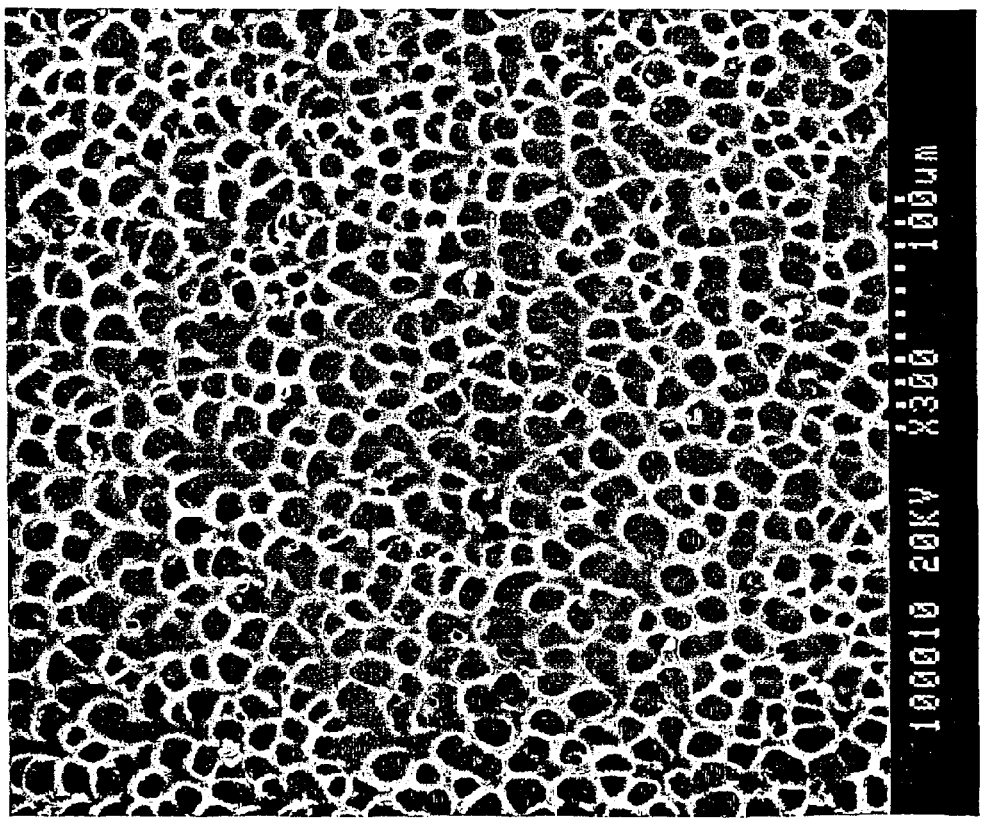
FIG. 16a shows a SEM micrograph of the inner lumen of a tube with a rough inner surface produced with the mixture formulation of 28.3% HEMA, 58.3% water, 5.3% MMA, 8.3% ethylene glycol, 0.15% APS, 0.12% SMBS, 2700 rpm (also listed in Table 1 as example 15)

Dimpled/rough surface morphology on the inner layer of a tube, which can be made using the mixture formulation listed in Table 1 as example 15, can be manufactured with the same methodology as Example 1. A tube with a dimpled/rough inner surface is shown in FIG. 16a. A lateral cross-section of the tube showing a gel-like/porous wall morphology and a dimpled/rough inner surface is shown in FIG. 16b.

EXAMPLE 16

Figure 17B:
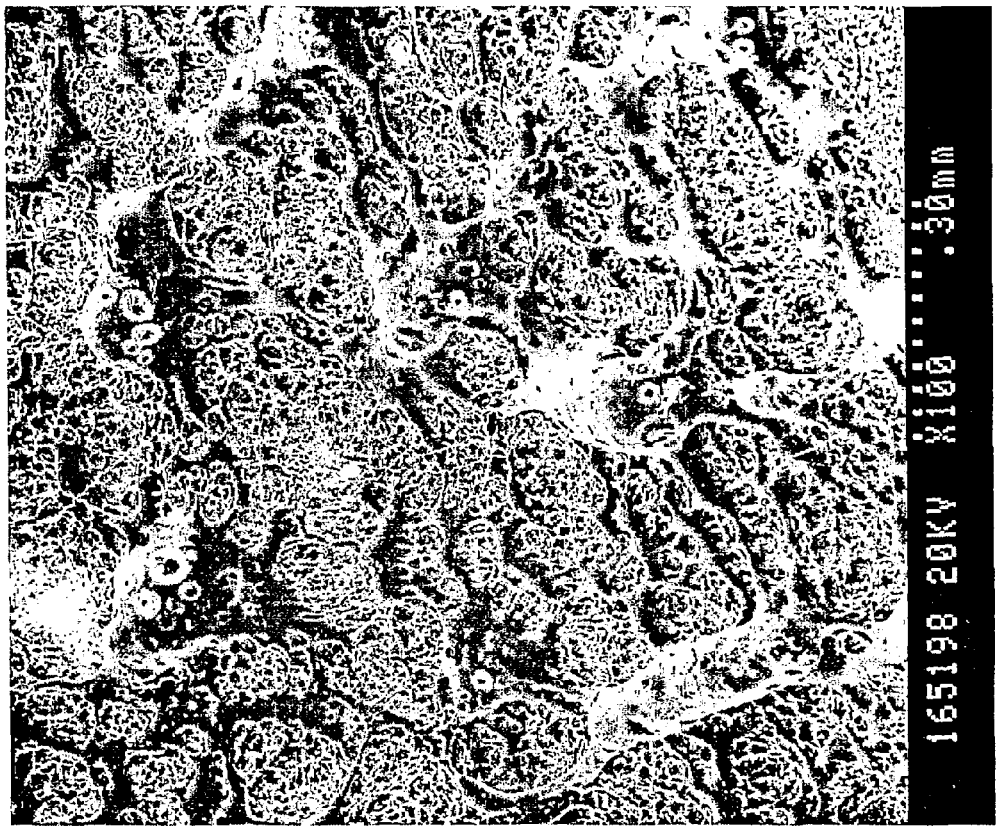
Figure 17A:
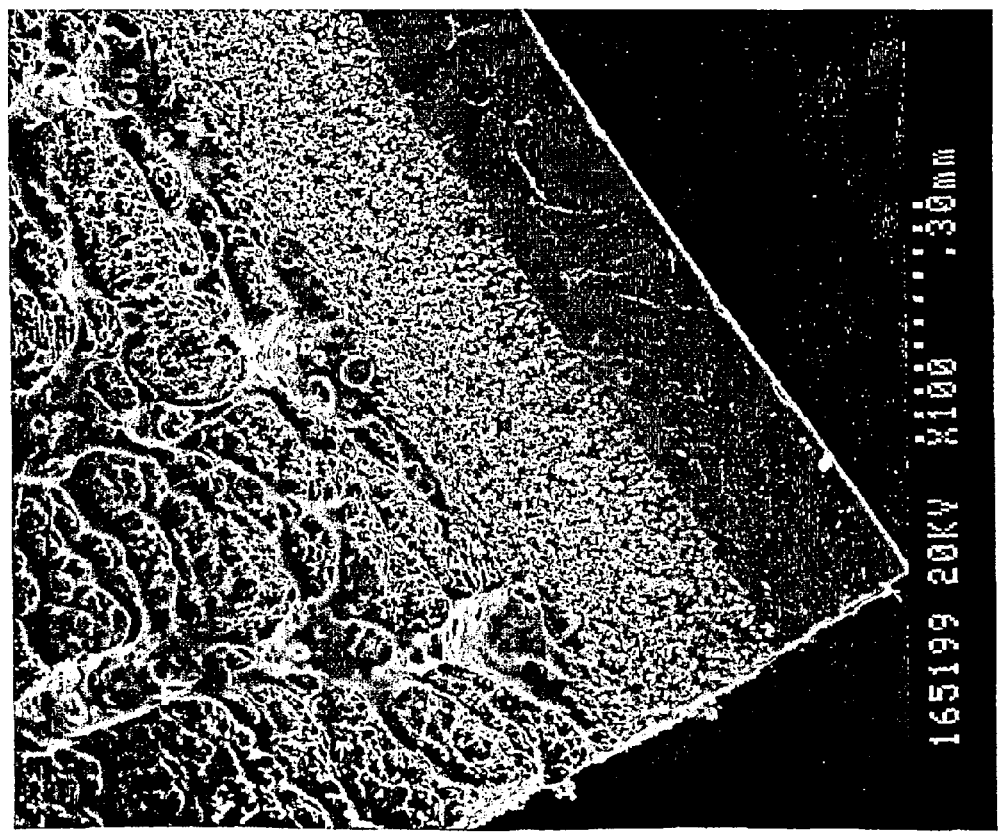
FIG. 17a shows a SEM micrograph of a lateral cross-section of the wall of the tube near the mold/polymer interface showing a gel-like/porous wall morphology and a unique cell-like surface pattern on the inner surface produced with a formulation of 27.3% HEMA, 2.7% MMA, 70% water, 0.03% EDMA, 0.12% APS, 0.09% SMBS, 4000 rpm (also listed in Table 1 as example 16)

Unique surface morphology of the inner lumen of a tube with unique cell-like surface patterns can be made using the mixture formulation listed in Table 1 as example 16 manufactured with the same methodology as Example 1. Surface morphologies such as those seen in FIG. 17a are created using this process. FIG. 17b shows such cell-like surface patterns on the inner lumen of a tube with a gel-like/porous wall morphology.

EXAMPLE 17

Figure 18:
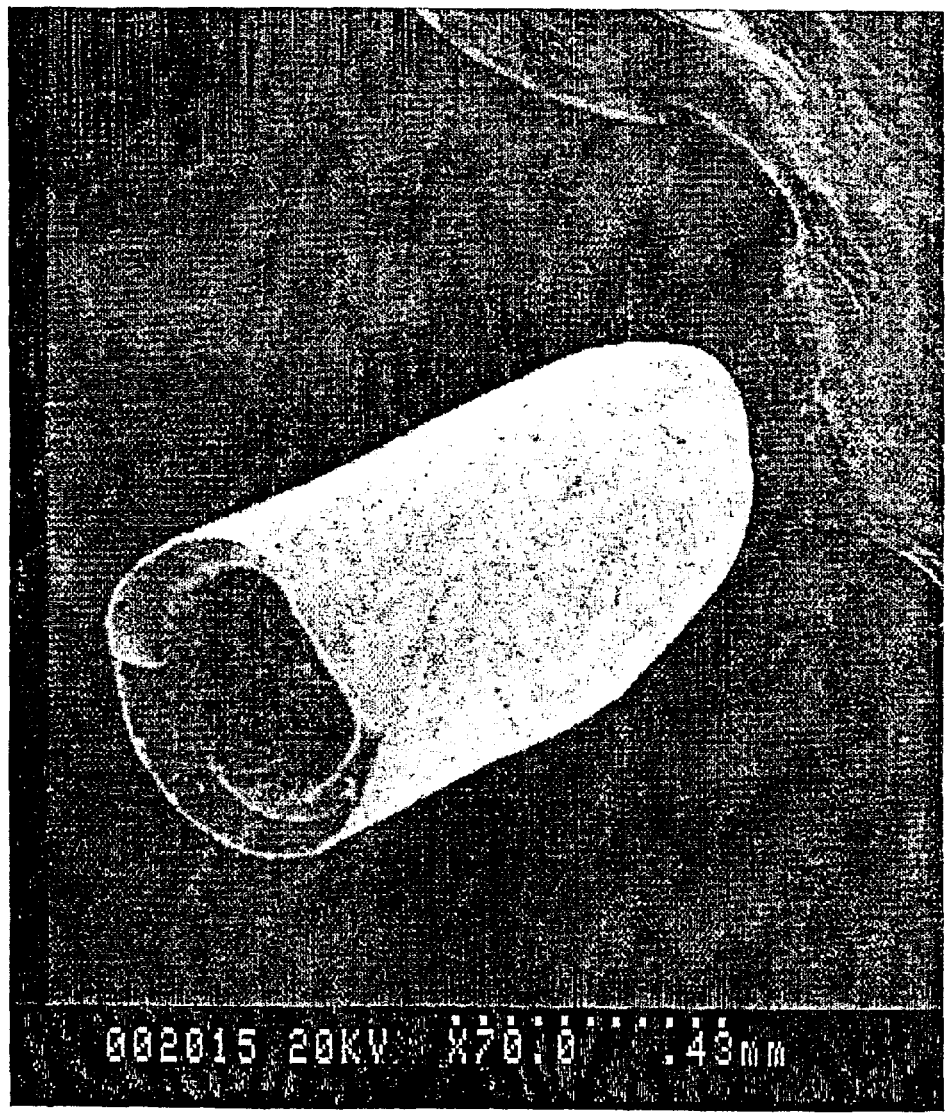
FIG. 18 shows a SEM micrograph of very small diameter micro-tubes manufactured with the mixture formulation of 22.5% HEMA, 2.5%MMA, 75% water, 0.125% APS, 0.1% SMBS, 4000 rpm (also listed in Table 1 as example 17), made in small diameter capillary tubing with an internal diameter of 450 $\mu$m.

Very small diameter micro-tubes can be manufactured with the same methodology as Example 1, except the mold size is very narrow. FIG. 18 is a tube that was manufactured from a mixture formulation listed in Table 1 as example 17 in small diameter capillary tubing with an internal diameter of 450 µm. Smaller tubing can be created by using molds with an internal diameter of 10 µm and larger.

EXAMPLE 18

Figure 19:
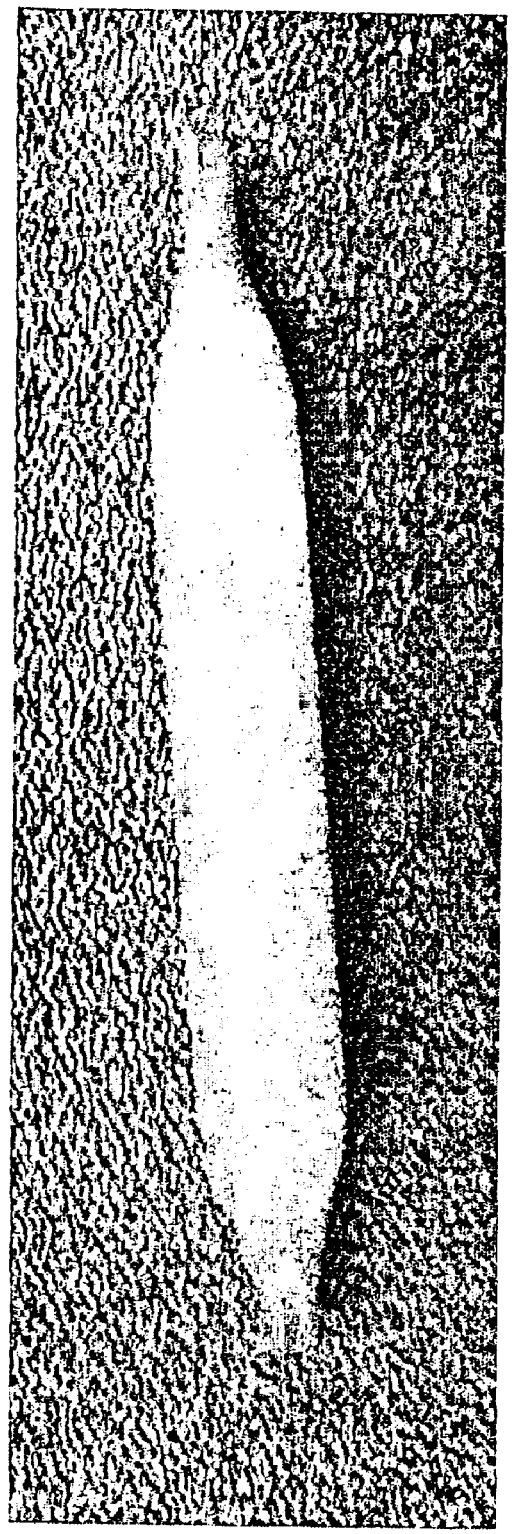
FIG. 19 is an optical micrograph of a non-uniformly shaped structure manufactured with the mixture formulation of 23.25% HEMA, 1.75% MMA, 75% water, 0.125% APS, 0.1% SMBS, 2500 rpm (also listed in Table 1 as example 17) wherein the mold size does not have a uniform internal diameter.

Various shaped structures can be manufactured with the same methodology as Example 1, except the mold size is neither cylindrical nor has a uniform internal diameter. FIG. 19 is a tube that was manufactured from a mixture formulation listed in Table 1 as example 18, in a mold with a variable diameter. Any example formulation can be used to create this shape of hollow structure.

EXAMPLE 19

A tapered hollow structure with changing dimensions along it length can be manufactured with the same methodology as example 1, except the sealed mold was placed into the chuck of a drill that had been mounted at a predetermined angle between 0 and 90° from the horizontal plane.

EXAMPLE 20

A hollow structure with variable wall thickness or holes along the length can be manufactured with the same methodology as example 1, except the sealed mold has some inner surface morphologies, such as in FIG. 2a–d. Any example formulation can be used to create this shape of hollow structure.

EXAMPLE 21

Hollow structures can be manufactured from the liquid-liquid phase separation of a polymer solution using temperature as the phase separating agent. Poly(lactic-co-glycolic acid) was dissolved in a 87:13 (wt %) dioxane/water mixture at 60° C. to create a solution that is injected into pre-heated glass molds. After injecting in a sealed glass mold, removing all air from the mold, it was placed in the chuck of a drill at room temperature and spun at 4000 rpm. The mold was allowed to cool to room temperature, which induced liquid-liquid phase separation and gelation. The mold was then frozen and the dioxane/water mixture removed by placing in a freeze-dryer. The formed tube is then removed from the mold.

EXAMPLE 22

N-2-(hydroxypropyl) methacrylamide (HPMA) (30 vol %) was polymerized in the presence of excess acetone/ dimethyl sulfoxide (DMSO) (93:7 v/v), with a crosslinking agent, preferably, but not limited to methylene bisacrylamide (1 mol %), using azobisisobutyronitrile (AIBN) as an initiating system. A monomeric sugar may or may not be also added to the polymerization mixture. The mixture was fully mixed, and injected into a cylindrical glass mold as described for Example 1 using the mixture formulation listed in Table 1 as example 22.

The sealed mold was placed in the chuck of a stirring drill that had been mounted horizontally, using a spirit level and rotated at 4000 rpm at 50° C. for 24 hours. The resulting hollow structure on the inner surface of the mold is removed from the mold.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

that deposits onto the inner surface includes at least the monomer, and wherein the step of stabilizing said deposited phase includes gelation of the monomer by polymerization thereof.

4. The process according to claim 3 wherein said phase separation agent is selected from the group consisting of light, pH, initiation agents, change in temperature, creation of a chemical product within the mold, changes in cationic and/or anionic concentrations, electric and magnetic fields.

5. The process according to claim 4 wherein said initiation agent is selected from the group consisting of free radical initiators, thermal and photo initiators and redox initiators.

6. The process according to claim 1 wherein said at least two components includes at least one polymer dissolved in at least one solvent, and wherein said solution is a substantially homogenous solution, wherein said at least one of the phases that deposits on the inner surface includes at least the polymer, and wherein the step of stabilizing said deposited phase includes gelation thereof.

7. The process according to claim 6 wherein said phase separation agent is selected from the group consisting of

TABLE 1

Example Fmulations

| Example # | Monomer 1 | Monomer 2 | Monomer 3 | Solvent 1 | Solvent 2 | Initiator 1 | Accelerator | Rotation | Tube ID |
|---|---|---|---|---|---|---|---|---|---|
| 1 | 1% HEMA | | | 99% water | | 0.01% APS | 0.01% SMBS | 4000 rpm | 2.4 mm |
| 2 | 1.9% HEMA | 0.1% PEGMA | | 98% water | | 0.02% APS | 0.02% SMBS | 2700 rpm | 3.2 mm |
| 3 | 7% HEMA | | | 93% water | | 0.05% APS | 0.04% SMBS | 4000 rpm | 7.5 mm |
| 4 | 15.75% HEMA | 2.25% MMA | 0.02% EDMA | 82% water | | 0.08% APS | 0.06% SMBS | 2700 rpm | 3.2 mm |
| 5 | 20% HEMA | 0.06% EDMA | | 80% water | | 0.1% APS | 0.04% TEMED | 2700 rpm | 2.4 mm |
| 6 | 20% HEMA | | 0.02% EDMA | 80% water | | 0.1% APS | 0.06% SMBS | 10000 rpm | 2.4 mm |
| 7 | 23.25% HEMA | 1.75% MMA | | 75% water | | 0.125% APS | 0.1% SMBS | 2500 rpm | 3.2 mm |
| 8 | 28.3% HEMA | 5.3% MMA | | 58.3% water | 8.3% EG | 0.125% APS | 0.1% SMBS | 2700 rpm | 1.8 mm |
| 9 | 27% HEMA | 3% MMA | | 70% water | | 0.1 APS | 0.075% SMBS | 4000 rpm | 2.4 mm |
| 10 | 27% HEMA | 3% MMA | | 70% water | | 0.15% APS | 0.12% SMBS | 2700 rpm | 2.4 mm |
| 11 | 20% HEMA | | | 80% water | | 0.1% APS | 0.4% SMBS | 2700 rpm | 3.2 mm |
| 12 | 2% HEMA | | | 98% water | | 0.02% APS | 0.02% SMBS | 30 rpm | 3.2 mm |
| 13 (o) | 1.8% HEMA | 0.2% PEGMA | | 98% water | | 0.002% APS | 0.002% SMBS | 2700 rpm | 3.2 mm |
| 13 (i) | 27% HEMA | | 3% MMA | 70% water | | 0.12% APS | 0.09% SMBS | 4000 rpm | |
| 14 | 20% HEMA | | 0.02% EDMA | 80% water | | 0.1% APS | 0.04% SMBS | 2700 rpm | 2.4 mm |
| 15 | 28.3% HEMA | 5.3% MMA | | 58.3% water | 8.3% EG | 0.15% APS | 0.12% SMBS | 2700 rpm | 1.8 mm |
| 16 | 27.3% HEMA | 2.7% MMA | 0.03% EDMA | 70% water | | 0.12% APS | 0.09% SMBS | 4000 rpm | 3.2 mm |
| 17 | 22.5% HEMA | 2.5% MMA | | 75% water | | 0.125% APS | 0.1% SMBS | 4000 rpm | 0.45 mm |
| 18 | 23.25% HEMA | 1.75% MMA | | 75% water | | 0.125% APS | 0.1% SMBS | 2500 rpm | 2.5 mm to 5.8 mm |
| 22 | 30 vol % HPMA | 1% MBAm | | 65% acetone | 4.9% DMSO | 1% AIBN | | 4000 rpm | 3.2 mm |

Therefore what is claimed is:

1. A process of producing a product, comprising:
   a) filling an interior of a mold with a solution so that substantially all air is displaced therefrom, the solution comprising at least two components which can be phase separated by a phase separation agent into at least two phases;
   b) rotating said mold containing said solution at an effective rotational velocity in the presence of said phase separation agent to induce phase separation between said at least two components into at least two phases so that under rotation at least one of the phases deposits onto an inner surface of the mold; and
   c) forming said product by stabilizing said at least one of the phases deposited onto the inner surface of the mold.

2. The process according to claim 1 including removing said product from said mold.

3. The process according to claim 1 wherein said at least two components includes at least one monomer and at least one solvent, and wherein said solution is a substantially homogenous solution, wherein said at least one of the phases light, change in pH, change in temperature, creation of a chemical product within the mold, changes in cationic and/or anionic concentrations, electric and magnetic fields.

8. The process according to claim 6 wherein gelation is achieved by exposure to an agent selected from the group consisting of light, change in pH, change in temperature, creation of a chemical product within the mold, changes in cationic and/or anionic concentrations, electric and magnetic fields.

9. The process according to claim 3 wherein said hollow mold is a cylindrical tube so that said product is a polymeric tube.

10. The process according to claim 9 wherein said cylindrical tube includes preselected surface features on said inner surface of the cylindrical tube.

11. The process according to claim 1 including inserting a porous structure into said mold prior to filling said mold with said solution, and wherein said product is coated on an outer surface of said porous structure.

12. The process according to claim 3 wherein said solution includes a cross-linking agent.

13. The process according to claim 12 wherein the crosslinking agent is selected from the group consisting of multifunctional methacrylate, acrylate, acrylamide, methacrylamide, 1,5-hexadiene-3,4-diol, 1,5-hexadiene (HD) multi-functional star polymers of poly(ethylene oxide).

14. The process according to claim 3 wherein said monomer is selected from the group consisting of acrylates, methacrylates, acrylic acid, methacrylic acid, acrylamide, methacrylamide and derivatives thereof; N-vinyl pyrrolidone, acenaphthalene, N-vinyl acetamide, phenylacetylene, acrolein, methyl acrolein, N-vinyl pyridine, vinyl acetate, vinyl chloride, vinyl fluoride, vinyl methyl ketone, vinylidene chloride, styrene and derivatives thereof, propene, acrylonitrile, methacrylonitrile, acryloyl chloride, allyl acetate, allyl chloride, allylbenzene, butadiene and derivatives thereof, N-vinyl caprolactam, N-vinyl carbazole, cinnamates and derivatives thereof, citraconimide and derivatives thereof, crotonic acid, diallyl phthalate, ethylene and derivatives thereof; fumarates and derivatives thereof, hexene and derivatives thereof, isoprene and derivatives thereof; itaconate and derivatives thereof; itaconamide and derivatives thereof; diethyl maleate, 2-(acryloyloxy)ethyl diethyl phosphate, vinyl phosphonates and derivatives thereof, maleic anhydride, maleimide, silicone monomers, and derivatives thereof; and any combination thereof.

15. The process according to claim 3 wherein said solvent is selected from the group consisting of nucleophilic or electrophilic molecules selected from the group consisting of water, alcohols, ethylene glycol, ethanol, acetone, poly (ethylene glycol), dimethyl sulfoxide, dimethyl formamide, alkanes and derivatives thereof, acetonitrile, acetic acid, benzene, acetic anhydride, benzyl acetate, carbon tetrachloride, chlorobenzene, n-butanol, 2-chloroethanol, chloroform, cyclohexane, cyclohexanol, dichloromethane, diethyl ether, di(ethylene glycol), di(ethylene glycol) monomethyl ether, 1,4-dioxane, N,N'-dimethyl acetamide, N,N'-dimethyl formamide, ethyl acetate, formaldehyde, n-heptane, hexachloroethane, hexane, isobutanol, isopropanol, methanol, methyl ethyl ketone, nitrobenzene, n-octane, n-pentanol, propyl acetate, propylene glycol, pyridine, tetrahydrofuran, toluene, trichloroethylene, o-xylene and p-xylene, a monomer, a liquid crosslinking agent, or mixtures thereof.

16. The process according to claim 3 wherein said solvent solubilizes said monomer but not a polymer or crosslinked polymer formed from said monomer.

17. The process according to claim 3 wherein said at least one monomer is present in a range from about 0.001% by weight to about 60% by weight.

18. The process according to claim 6 wherein said polymer is selected from the group consisting of polyacrylates, polysulfones, peptide sequences, proteins, oligopeptides, collagen, fibronectin, laminin, polymethacrylates, polyacetates, polyesters, polyamides, polycarbonates, polyanhydrides, polyamino acids, cellulose, hyaluronic acid, sodium hyaluronate, alginate, agarose, chitosan, chitin, and mixtures thereof.

19. The process according to claim 1 including physically or chemically modifying the inner surface of the mold upon which preselected morphologies are induced into the wall of the said product by inducing beading or spreading of the separated liquid phase.

20. The process according to claim 19 with molecules including silanating agents.

21. The process according to claim 3 including the step of removing the solvent and including repeating steps a), b) and c), at least once to produce a multi-layered product.

22. The method according to claim 9 wherein said polymeric tube has an internal diameter in a range from about 10 µm to about 100 cm.

23. The process according to claim 6 wherein said hollow mold is a cylindrical tube so that said product is a polymeric tube.

24. The process according to claim 2 wherein said at least two components includes at least one monomer and at least one solvent, and wherein said solution is a substantially homogenous solution, wherein said at least one of the phases that deposits onto the inner surface includes at least the monomer, and wherein the step of stabilizing said deposited phase includes gelation of the monomer by polymerization thereof.

25. The process according to claim 24 wherein said phase separation agent is selected from the group consisting of light, pH, initiation agents, change in temperature, creation of a chemical product within the mold, changes in cationic and/or anionic concentrations, electric and magnetic fields.

26. The process according to claim 25 wherein said initiation agent is selected from the group consisting of free radical initiators, thermal and photo initiators and redox initiators.

27. The process according to claim 2 wherein said at least two components includes at least one polymer dissolved in at least one solvent, and wherein said solution is a substantially homogenous solution, wherein said at least one of the phases that deposits on the inner surface includes at least the polymer, and wherein the step of stabilizing said deposited phase includes gelation thereof.

28. The process according to claim 27 wherein said phase separation agent is selected from the group consisting of light, change in pH, change in temperature, creation of a chemical product within the mold, changes in cationic and/or anionic concentrations, electric and magnetic fields.

29. The process according to claim 28 wherein gelation is achieved by exposure to an agent selected from the group consisting of light, change in pH, change in temperature, creation of a chemical product within the mold, changes in cationic and/or anionic concentrations, electric and magnetic fields.

30. The process according to claim 24 wherein said hollow mold is a cylindrical tube so that said product is a polymeric tube.

31. The process according to claim 27 wherein said hollow mold is a cylindrical tube so that said product is a polymeric tube.

32. The process according to claim 30 wherein said polymeric tube has an internal diameter in a range from about 10 µm to about 100 cm.

33. The process according to claim 31 wherein said polymeric tube has an internal diameter in a range from about 10 µm to about 100 cm.

34. The process according to claim 2 including inserting a porous structure into said mold prior to filling said mold with said solution, and wherein said product is coated on an outer surface of said porous structure.

35. The process according to claim 6 including the step of removing the solvent and including repeating steps a), b) and c), at least once to produce a multi-layered product.

36. The process according to claim 24 including the step of removing the solvent and including repeating steps a), b) and c), at least once to produce a multi-layered product.

37. The process according to claim 27 including the step of removing the solvent and including repeating steps a), b) and c), at least once to produce a multi-layered product.

38. The process according to claim 6 wherein said solution includes a cross-linking agent.

39. The process according to claim 6 wherein said solvent is selected from the group consisting of a nucleophilic or electrophilic molecule selected from the group of water, alcohols, ethylene glycol, ethanol, acetone, poly(ethylene glycol), dimethyl sulfoxide, dimethyl formamide, alkanes and derivatives thereof, acetonitrile, acetic acid, benzene, acetic anhydride, benzyl acetate, carbon tetrachloride, chlorobenzene, n-butanol, 2-chloroethanol, chloroform, cyclohexane, cyclohexanol, dichloromethane, diethyl ether, diethylene glycol, diethylene glycol monomethyl ether, 1,4-dioxane, N,N'-dimethyl acetamide, N,N'-dimethyl formamide, ethyl acetate, formaldehyde, n-heptane, hexachloroethane, hexane, isobutanol, isopropanol, methanol, methyl ethyl ketone, nitrobenzene, n-octane, n-pentanol, propyl acetate, propylene glycol, pyridene, tetrahydrofuran, toluene, trichloroethylene, o-xylene and p-xylene, a monomer, a liquid crosslinking agent, or mixtures thereof.

40. The process according to claim 12 wherein the crosslinking agent is selected from the group consisting of ethylene glycol dimethacrylate (EDMA), hexamethylene dimethacrylate (HDMA), poly(ethylene glycol) dimethacrylate, 2,3-dihydroxybutanediol 1,4-dimethacrylate (BHDMA) and 1,4-butanediol dimethacrylate (BDMA).

41. The process according to claim 3 wherein said monomer is selected from the group consisting of 2-hydroxyethyl methacrylate, methyl methacrylate, 2-polyethylene glycol ethyl methacrylate, ethyl acrylate, 2-hydroxyethyl acrylate, 2-chloroethyl methacrylate, butyl methacrylate, glycidyl methacrylate, hydroxypropyl methacrylate; hydroxypropyl methacrylamide, N,N-diethyl acrylamide, N,N-dimethyl acrylamide, 2-chloroethyl acrylamide, 2-nitrobutyl acrylamide; 1,1 diphenyl-ethylene, chlorotrifluoro-ethylene, dichloroethylene, tetrachloro-ethylene; isopropenyl acetate, isopropenyl methyl ketone, isopropenylisocyanate; and any combination thereof.

42. The process according to claim 6 wherein said polymer is selected from the group consisting of poly(methyl methacrylate), poly(ethoxyethyl methacrylate), poly(hydroxyethylmethacrylate); poly(N-vinyl pyrrolidinone), polyvinyl acetate, polyvinyl alcohol, poly(hydroxypropyl methacrylamide), poly(caprolactone), poly(dioxanone) polyglycolic acid, polylactic acid, copolymers of lactic and glycolic acids, and polytrimethylene carbonates, poly(butadiene), polystyrene, polyacrylonitrile, poly(chloroprene), neoprene, poly(isobutene), poly(isoprene), polypropylene, polytetrafluoroethylene, poly(vinylidene fluoride), poly(chlorotrifluoroethylene), poly(vinyl chloride), poly(oxymethylene), poly(ethylene terephthalate), poly(oxyethylene) poly(oxyterephthaloyl); poly[imino(1-oxohexamethylene)], poly(iminoadipoyl-iminohexamethalene), poly(iminohexamethylene-iminosebacoyl), poly[imino(1-oxododecamethylene)], and mixtures thereof.

* * * * *